(12) United States Patent
Goldstein et al.

(10) Patent No.: US 6,958,321 B2
(45) Date of Patent: Oct. 25, 2005

(54) ISOLATION, CHARACTERIZATION, CLONING AND USE OF A MUSHROOM LECTIN

(75) Inventors: Irwin J. Goldstein, Ann Arbor, MI (US); Harry C. Winter, Ann Arbor, MI (US); Robert P. Kruger, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 382 days.

(21) Appl. No.: 10/137,077

(22) Filed: May 2, 2002

(65) Prior Publication Data

US 2003/0092109 A1 May 15, 2003

Related U.S. Application Data

(60) Provisional application No. 60/354,322, filed on Feb. 4, 2002, and provisional application No. 60/288,596, filed on May 3, 2001.

(51) Int. Cl.[7] .................. C07K 17/00; A61K 38/16; G01N 21/76
(52) U.S. Cl. .................. 514/8; 530/350; 530/395; 530/413; 435/7.1; 436/172
(58) Field of Search .................. 514/8; 530/350, 530/395, 413; 436/172; 435/7.1

Primary Examiner—Karen Cochrane Carlson
Assistant Examiner—Samuel Wei Liu
(74) Attorney, Agent, or Firm—Medlen & Carroll, LLP

(57) ABSTRACT

The isolation, characterization, cloning and expression of the lectin (agglutinin) from *Marasmius oreades* (MOA) is described. MOA displays unique carbohydrate binding properties, including blood group B-specific agglutination and preferential binding to Gal$\alpha$1,3Gal-containing sugar epitopes, including but not limited to Gal$\alpha$1,3Gal$\beta$1, 4GlcNAc. MOA is contemplated as an affinity reagent, a therapeutic in the treatment of antibiotic-induced diarrhea and the field of xenotransplantation. MOA may also serve as a diagnostic reagent, e.g. for malaria.

6 Claims, 17 Drawing Sheets

(1 of 17 Drawing Sheet(s) Filed in Color)

```
  1 MSLRRGIYHIENAGVPSAIDLKDGSSSDGTPIVGWQFTPDTINWHQLWLAEPIPNVADTFTLCNLFS
                                    1-4
 68 GTYMDLYNGSSEAGTAVNGWQGTAFTNPHQLWTIKKSSDGTSYKIQNYGSKTFVDLVNGDSSD
                  7
132 GAKIAGWTGTWDEGNPHQKWYFNRMSVSSAEQAAIARNPHIHGTYRGYILDGEYLVLPNATFT
              8                        5
196 QIWKDSGLPGSKWREQIYDCDDFAIAMKAAVGKWGADSWKANGFAIFCGVMLGVNKAGDAAH
                                     6
258 AVNFTLTKDHADIVFEPQNGG

1   MSLRRGIYHIENAGVPSAIDLKDGSSSDGTPIVGWQFTPDTINWHQLWLAEPIPNVADTFTLCNLFS
                                        1-4
68  GTYMDLYNGSSEAGTAVNGWQGTAFTTNPHQLWTIKKSSDGTSYKIQNYGSKTFVDLVNGDSSD
                  7
132 GAKIAGWTGTWDEGNPHQKWYFNRMSVSSAEAQAAIARNPHIHGTYRGYILDGEYLVLPNATFT
               8                                 5
196 QIWKNSGLPGSKWREQIYDCDDFAIAMKAAVGKWGADSWKANGFAIFCGVMLGVNKAGDAAH
                                6
258 AYNFTLTKDHADIVFFEPQNGGYLNDIGYDSYMAFY   SEQ ID NO: 3

FIG. 2

ATCGTTTCTTAACAACTCTCAGCTCCAAGCCTCCACTACTCGTAACTAACTGA
AA<u>ATG</u>TCTCTGCGACGCGGAATTTACCACATCGAGAATGCTGGGGTTCCCAG
TGCCATTGATCTCAAAGACGGCAGCTCCAGTGACGGCACACCTATCGTTGGC
TGGCAGTTTACACCAGACACGATCAACTGGCATCAGCTCTGGCTTGCTGAAC
CAATCCCCAACGTTGCTGATACCTTTACCCTTTGCAACCTGTTCAGCGGTACC
TACATGGATCTCTACAACGGTTCTTCCGAAGCGGGCACCGCAGTCAATGGTT
GGCAAGGAACTGCCTTTACGACCAATCCCCACCAGCTCTGGACCATCAAGAA
GTCGAGCGACGGTACGAGCTACAAGATCCAGAATTATGGAAGTAAAACCTTC
GTCGATCTTGTCAATGGCGACAGCTCTGATGGGGCCAAAATTGCTGGATGGA
CCGGCACTTGGGATGAAGGTAACCCTCACCAGAAATGGTACTTCAATAGGAT
GAGCGTCTCCAGCGCGGAGGCCCAAGCGGCTATCGCGCGAAACCCTCATATT
CATGGGACTTACAGAGGATACATCCTCGATGGAGAATATCTTGTCCTCCCTAA
CGCTACTTTCACGCAGATTTGGAAAGACTCCGGTCTTCCTGGTAGCAAATGGC
GTGAGCAAATCTATGATTGCGATGACTTTGCTATAGCCATGAAGGCCGCCGTT
GGGAAGTGGGGCGCCGACTCCTGGAAGGCTAATGGCTTCGCCATCTTTTGTG
GAGTTATGCTTGGTGTCAACAAGGCTGGAGATGCGGCCCATGCTTACAACTT
CACCCTCACCAAGGACCATGCTGACATTGTCTTCTTTGAGCCTCAGAACGGTG
GATACCTGAACGACATTGGCTATGACAGCTACATGGCCTTCTAC<u>TGA</u>AGGGA
CGGGTGAAAAGACCTGTTAYGATRCGAAATGTACAGTCCAAGAGAAAAAGA
CGGAAAAAAACCGCGTGTACCAGATGTCCGATAAACAGTCATATGTATAATC
CAGATACTCGATTTACT

FIG. 3

```
ricin 1α    11   VRIVGRNG--LCVDVRDGRFHNGNAIQLWPCKSNT-DANQLWTLKRD     54  SEQ ID NO: 17
ricin 2γ   222   GTILNLYSG-LVLDVRASDPSLKQ-IILYPLHGD---PNQIWLPLF    263  SEQ ID NO: 18
ebulin 1α   12   TRRIVGRDG--LCVDVRNGYDTDGTPIQLWPCGTQ---RNQQWTFYNDKT  57  SEQ ID NO: 19
ebulin 2γ  223   GSVVNLKST-RVMDVKESDVSLQE-VIEPATGN---PNQQWRTQV      264  SEQ ID NO: 20
MOA α        7   IYHIENAGVPSAIDLKDGSSSDGTPIVGWQFTPDTINWHQLWLAEPIPNVA  57  SEQ ID NO: 21
MOA β       58   DTFTLCNLFSGTYMDLYNGSSEAGTAVNGWQGTAFTTNPHQLWTIKKSDSG 108  SEQ ID NO: 22
MOA γ      109   TSYKIQNYGSKTFVDLVNGDSSDGAKIAGWTGTWDEGNPHQKWYFNR    155  SEQ ID NO: 23
                                                  loop
                                                 region
```

FIG. 4

ISOLATION, CHARACTERIZATION, CLONING AND USE OF A MUSHROOM LECTIN

PRIORITY

This application claims the benefit of U.S. Provisional Application Ser. No. 60/288,596, filed on May 3, 2001 and U.S. Provisional Application Ser. No. 60/354,322, filed on Feb. 4, 2002.

STATEMENT OF GOVERNMENTAL INTEREST

This invention was made with government support awarded by the National Institutes of Health under grant number GM 29470-35. The Government has certain rights in the invention.

FIELD OF THE INVENTION

The invention relates to the field of carbohydrate binding proteins, and more specifically a protein which binds specifically to particular oligosaccharides associated with particular medical significance.

BACKGROUND

The Galα1,3Gal epitope has received considerable attention stemming from its presence in glycoproteins of most mammals and its conspicuous absence in humans, apes, and Old World monkeys. The loss is attributable to frameshift mutations in α,3-galactosyltransferase and the resulting immunogenicity of the epitope is a significant barrier to xenotransplantation.

There are a few proteins that bind the Galα,3Gal epitope. For example, antibodies which recognize the α-galactosyl epitope and *Clostridium difficile* toxin A both bind well to some Galα1,3Gal-containing sugars. However, merely binding to this epitope is not useful if the same protein binds many other related epitopes.

What is needed is a protein which binds the Galα1,3Gal epitope with specificity so that it can be useful in binding assays, including diagnostic assays.

SUMMARY OF THE INVENTION

In some embodiments, a method is contemplated, comprising: a) providing: (i) *M. oreades* mushrooms, and (ii) an extraction buffer comprising a protease inhibitor cocktail and ethylenediaminetetraacetic acid; b) preparing an extract of said *M. oreades* mushrooms in said extraction buffer; and c) treating said extract under conditions such that a lectin preparation is produced. In some embodiments, said preparing step b) is carried out under an atmosphere of argon. In some embodiments, said treating step c) comprises column chromatography. In some embodiments, said column chromatography comprises a melibiose-Sepharose affinity column.

In some embodiments, an additional purification step d) passing said lectin preparation through an affinity column to produce a purified lectin is contemplated. In some embodiments, said affinity column of step d) comprises G1α1,3 [L-Fucα1,2]Galβ$O(CH_2)_n$CONH. In some embodiments, said lectin produced by passing said lectin preparation through an affinity column has high binding affinity for G1α1,3Ga1. In some embodiments, the lectin preparation is substantially free of proteolytic fragments of said lectin. In some embodiments, said binding affinity is determined by a method selected from the group consisting of isothermal titration calorimetry, blood cell agglutination and carbohydrate precipitation. Binding affinity of the lectin preparation and the purified lectin may be determined by a method selected from the group consisting of isothermal titration calorimetry, blood cell agglutination and carbohydrate precipitation. In some embodiments, a composition comprising the purified lectin is contemplated.

In some embodiments, a method is contemplated, comprising: a) providing: (i) a composition comprising labeled *M. oreades* agglutinin, and (ii) a sample obtained from a subject; and b) contacting said sample with said labeled *M. oreades* agglutinin under conditions such that a glycoconjugate in said sample is detected. It is not intended that the method be limited to any particular method of preparation of said *M. oreades* agglutinin for labeling and use in the method. A variety of *M. oreades* agglutinin preparations are contemplated. In some embodiments, recombinantly produced *M. oreades* agglutinin is contemplated. In some embodiments, biochemically purified *M. oreades* agglutinin is contemplated. In some embodiments, said biochemically purified *M. oreades* agglutinin is substantially free of proteolytic fragments, including fragments of approximately 23 kDa and approximately 10 kDa. In some embodiments, a biochemically prepared *M. oreades* agglutination preparation comprising proteolytic fragments is contemplated. In some embodiments, said subject has one or more symptoms of malaria. In some embodiments, said sample is a human blood sample. In some embodiments, said human blood sample comprises *Plasmodium falciparum* merozoites. In some embodiments, said labeled *M. oreades* agglutinin comprises a fluorescent label. In some embodiments, said fluorescent label is fluorescein.

In some embodiments, a composition comprising immobilized *M. oreades* agglutinin is contemplated. It is not intended that the composition be limited to any particular method of preparation of said *M. oreades* agglutinin for immobilization. A variety of *M. oreades* agglutinin preparations are contemplated. In some embodiments, recombinantly produced *M. oreades* agglutinin is contemplated. In some embodiments, biochemically purified *M. oreades* agglutinin is contemplated. In some embodiments, said biochemically purified *M. oreades* agglutinin is substantially free of proteolytic fragments, including fragments of approximately 23 kDa and approximately 10 kDa. In some embodiments, a biochemically prepared *M. oreades* agglutination preparation comprising proteolytic fragments is contemplated. In some embodiments, said immobilized *M. oreades* agglutinin is immobilized on Sepharose 4B. In some embodiments, said Sepharose 4B-immobilized *M. oreades* agglutinin is contained in a column.

In some embodiments, a method is contemplated, comprising: a) providing: i) an immobilized-*M. oreades* agglutinin affinity column, ii) a sample suspected of comprising a saccharide selected from the group consisting of G1α1, 3Ga1, G1α1,3Ga1β1,4G1cNAc and G1α1,3 [L-Fucα1,2] Ga1; b) contacting said sample with said affinity column under conditions such that said saccharide is bound in a complex; and c) treating said complex under conditions such that said saccharide is released from said complex. It is not intended that the method be limited to any particular method of preparation of said *M. oreades* agglutinin for immobilization and use in the affinity column of the method. A variety of *M. oreades* agglutinin preparations are contemplated. In some embodiments, recombinantly produced *M. oreades* agglutinin is contemplated. In some embodiments, biochemically purified *M. oreades* agglutinin is contemplated.

In some embodiments, said biochemically purified *M. oreades* agglutinin is substantially free of proteolytic fragments, including fragments of approximately 23 kDa and approximately 10 kDa. In some embodiments, a biochemically prepared *M. oreades* agglutination preparation comprising proteolytic fragments is contemplated. In some embodiments, said sample is a serum sample.

In some embodiments, a composition comprising an isolated nucleic acid having the sequence of SEQ ID NO: 1 is contemplated. In some embodiments, a vector comprising the isolated nucleic acid having the sequence of SEQ ID NO: 1 is contemplated. In some embodiments, said vector is an expression vector. In some embodiments, said nucleic acid sequence is operably linked to an inducible promoted in said expression vector. In some embodiments, a cell comprising an expression vector comprising a nucleic acid having the sequence of SEQ ID NO: 1 is contemplated. In some embodiments, said cell is a bacterial cell. In some embodiments, said bacterial cell further comprises the protein encoded by the nucleic acid having the sequence of SEQ ID NO: 1. In some embodiments, a composition comprising purified DNA having the nucleotide sequence of SEQ ID NO: 1 is contemplated. In some embodiments, RNA transcribed from said DNA is contemplated. In some embodiments, protein translated from said RNA is contemplated. In some embodiments, antibodies produced against said protein are contemplated. In some embodiments, transgenic animals comprising the DNA having the nucleotide sequence of SEQ ID NO: 1 are contemplated. In some embodiments, a vector comprising DNA having the nucleotide sequence of SEQ ID NO: 1 is contemplated. In some embodiments, said vector is an expression vector. In some embodiments, cells comprising said expression vector are contemplated. In some embodiments, said cells are selected from the group consisting of bacterial cells, yeast ells, insect cells and mammalian cells. In a preferred embodiment, said cells are bacterial cells. In some embodiments, a composition comprising an isolated polypeptide having the sequence of SEQ ID NO: 2 is contemplated. In some embodiments, a composition comprising an isolated polypeptide having the sequence of SEQ ID NO: 3 is contemplated.

Specificity varies greatly among carbohydrate binding proteins. While some lectins broadly recognize all oligosaccharides containing particular terminal sugars, others show increasing affinity for specific di- and tri-saccharides. Fewer still show almost no reactivity with a given sugar monomer, yet bind strongly and specifically to particular oligosaccharides. The present invention contemplates a protein, MOA, which binds to G1α1,3Ga1-containing sugars with specificity. In a preferred embodiment, the protein is isolated from a mushroom, such as *M. oreades* (which can be purchased from American Mushroom Hunter Corp. (Middle Town, N.J.).

In one embodiment, the protein is purified biochemically. In a preferred embodiment, a protease inhibitor cocktail (e.g. product P8215) is included during the extraction procedure at the level of at least 1 ml/L extract buffer in place of phenylmethylsulfonyl fluoride, eliminating $Ca^{++}$ and including at least 1.25 mM EDTA in all buffers. Ideally, the extraction and ammonium sulfate precipitations are performed under an atmosphere of argon. Such a procedure minimizes proteolysis and yields a protein monomer (whereas proteolysis can create a dimer or trimer).

In a preferred embodiment, the protein is recombinant and expressed in a transfected host cell. A variety of host cells are contemplated including but not limited to bacterial cells, insect cells and mammalian cells. On the other hand, the protein can also be prepared without host cells using a coupled in vitro transcription/translation kit (available commercially from Promega, Madison Wis.).

In one embodiment, the present invention contemplates the protein having the amino acid sequence shown in "SEQ ID NO:2 shown in FIG. 1A". In another embodiment, the present invention contemplates the protein having the amino acid sequence shown in "SEQ ID NO: 3 shown in FIG. 2". On the other hand, proteins having conservative amino acid substitutions in this sequence are also contemplated. For example, one skilled in the art understand that certain amino acids can be readily substituted with no significant loss in activity (e.g. isoleucine for leucine, etc.). One skilled in the art will understand that some sequences may be polymorphic and polymorphisms in the amino acid sequence shown in FIG. 1A are contemplated. One such polymorphic sequence is shown in FIG. 2 [SEQ ID NO:3].

Whether prepared biochemically or recombinantly, the present invention contemplates labeling the protein (e.g. with a radiolabel, fluorescent label, etc.). In one embodiment, fluorescein-labeled MOA protein is provided. In one embodiment, fluorescein-labeled MOA is used in a method comprising; a) providing (i) labeled MOA and (ii) a blood smear, and (b) contacting said blood smear with said labeled MOA; and (c) examining said contacted smear for the presence of labeled MOA. In one embodiment, said blood smear is from a subject exhibiting one or more symptoms of malaria. In one embodiment, said blood smear is from a subject suspected of having malaria. In one embodiment, said presence of said labeled MOA in said examining step (c) is diagnostic of the presence of *Plasmodium falciparum* merozoites. In another embodiment, the present invention contemplates immobilizing the protein (e.g. on a resin for affinity purification of carbohydrate containing molecules, on beads for binding to cells, etc.). In one embodiment, said immobilization is on Sepharose B beads. In one embodiment, said immobilized MOA protein is used as an affinity reagent for isolation of carbohydrate containing molecules. In one embodiment, said carbohydrate containing molecules comprise a Gala 1,3Ga1 epitope. In one embodiment, affinity purification of a carbohydrate epitope from *Plasmodium falciparum* merozoites is contemplated.

The present invention contemplates the protein (or portions thereof) encoded by the nucleic acid sequence shown in FIG. 3. This nucleic acid sequence can be readily inserted in a variety of vectors for expression. Therefore, the present invention contemplates vectors comprising the nucleic acid sequence shown in "SEQ ID NO: 1 shown in FIG. 3" as well as host cells containing such a vector and the product of such host cells.

The present invention contemplates methods wherein the biochemically produced protein monomer or the recombinant protein are used for binding. It is not intended that the method of biochemically producing the protein be limiting. In some embodiments, biochemical methods are used to produce a *M. oreades* agglutinin preparation comprising proteolytic fragments of approximately 23 kDa and 10 kDa. In some embodiments, biochemical methods are used to purify the *M. oreades* agglutinin such that the preparation is substantially free of proteolytic fragments (including fragments of approximately 23 kDa and 10 kDa). Binding can be used for blood testing. In one embodiment, said blood testing is to detect the presence of *Plasmodium falciparum* merozoites. On the other hand, binding can be done to mask an immunogenic epitope on a tissue for transplantation.

Furthermore, binding can be used to detect a microorganism (e.g. binding to the plasmodium of malaria) or cancer cell. Finally, binding can be used to cause disease (e.g. administration of the protein to cause a kidney pathology).

In some embodiments, the present invention provides a novel lectin (i.e. agglutinin) isolated from *Marasmius oreades* (hereinafter "MOA"). The lectin, MOA, has a high binding affinity for Gala 1,3Ga1 end groups and is specific for the α 1,3-linkage. MOA does not bind the isomeric a 1,4 and a 1,6-disaccharides or individual sugar residues. In preferred embodiments, intact MOA is isolated as polypeptide of approximately 33 kDa. Ideally, the 33 kDa protein is purified so as to be substantially free of proteolytic fragments.

In some embodiments, the present invention also provides methods for using MOA. It can be used as a research tool to detect the presence of and characterize di- and tri-saccharides having at least one Gala 1,3Ga1 unit present. An immobilized form of MOA can be used to isolate glycoconjugates, polysaccharides or oligosaccharides or to resolve mixtures containing molecules having at least one Gala 1,3Ga1 unit present. Therapeutic methods are also provided. MOA can be used to block transplant rejection of porcine tissue in humans. Porcine tissues and organs contain the Galα1,3Ga1β1,4G1cNAc epitope which is not found in humans and is involved in tissue rejection. Binding of MOA to this epitope would block recognition by the immune system and thereby block transplant rejection. The present invention further provides methods for blocking the action of Toxin A from *Clostridium difficile* which is responsible for antibiotic-induced diarrhea. Both MOA and Toxin A recognize the same trisaccharide epitope, Galα1,3Ga1↑1, 4G1cNAc. A patient taking antibiotics or suffering from diarrhea caused by Toxin A can be treated with a therapeutically effective amount of MOA. MOA would then compete with Toxin A to bind the target cells, preventing Toxin A from causing any symptoms.

DESCRIPTION OF THE FIGURES

The file of this patent contains at least one drawing executed in color. Copies of this patent with color drawings will be provided by the Patent and Trademark Office upon request and payment of the necessary fee.

FIG. 1A shows a derived full-length MOA amino acid sequence [SEQ ID NO: 2]. Underlined regions denote position of the MOA peptides sequence during the cloning (Table 1; SEQ ID NOs: 9–16). The boxed region shares homology with the ricin B chain lectin domain. FIG. 1B shows an alignment of a portion of the MOA amino acid sequence [SEQ ID NO: 4] with an assortment of bacterial toxins and carbohydrate degrading enzymes [SEQ ID NOs: 5–8]. Three conserved QXW/F motifs (each identified with a line) are noted. Residues that are identical to the consensus sequence are boxed and shaded. Residues that are similar to the consensus are shaded. Numbers indicate the amino acid positions of the selected full-length sequences.

FIG. 2 shows the predicted amino acid sequence of a polymorphic form of MOA [SEQ ID NO: 3]

FIG. 3 shows the cDNA sequence (SEQ ID NO: 1) encoding the MOA protein (with the coding region defined by underlining).

FIG. 4 shows an alignment of MOA subdomains with the ricin and ebulin subdomains that bind galactose [SEQ ID NOs: 17–23]. Key residues that hydrogen bond with the galactosyl third and fourth oxygens are denoted with triangles. The key sugar stacking residue is denoted with a star. The loop region referenced in the text is also labeled. Residues that are identical to the consensus sequence are boxed and shaded. Residues that are similar to the consensus are shaded. Numbers indicate the amino acid positions of the selected full-length sequences.

Definitions

Figure 5:
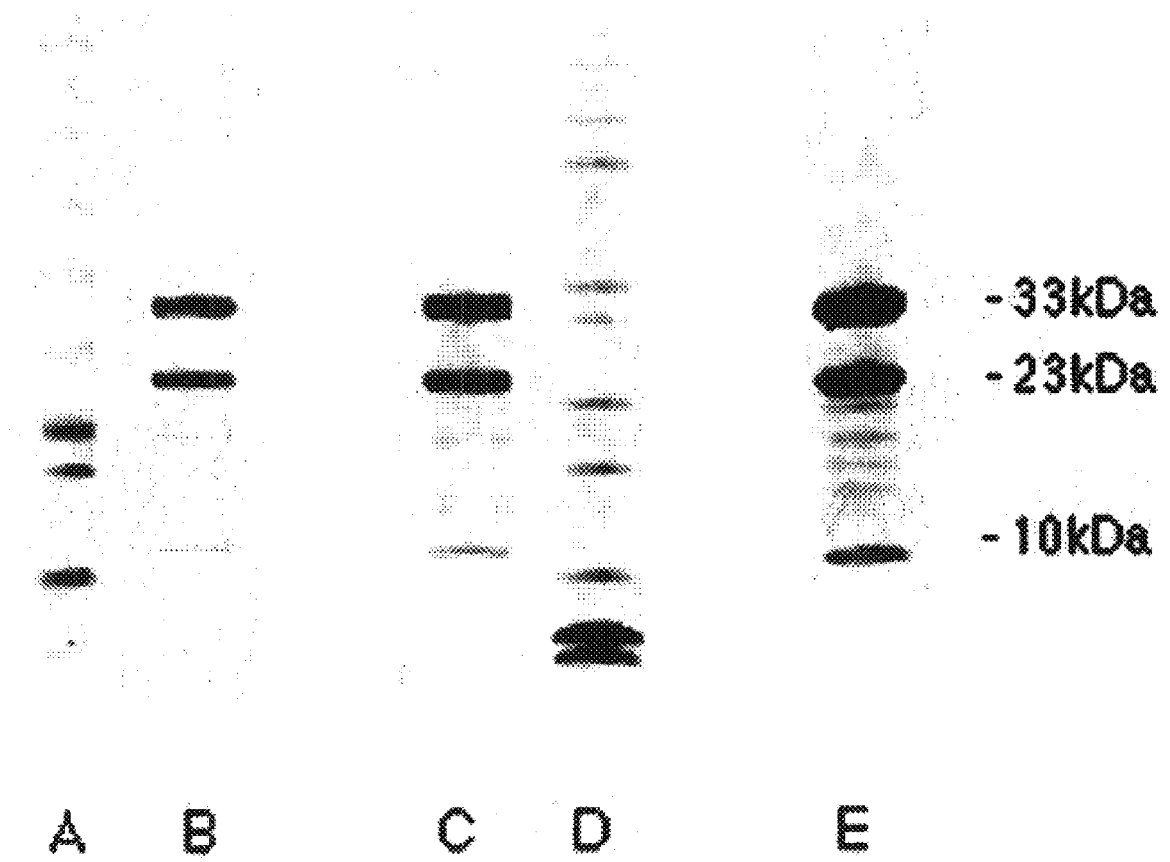
FIG. 5 shows SDS-PAGE analysis of MOA prepared by the method of Example 1. Lanes B, C and E contain 5, 10 and 20 μg (respectively) of purified MOA. Lanes A and D contain low molecular weight protein standards.

In order to facilitate an understanding of the invention, a number of terms are defined below.

As used herein a "protease inhibitor cocktail" is a composition comprising one or more protease inhibitors. Protease inhibitor cocktails may be purchased from commercial sources, including but not limited to Product P8215 from Sigma (St. Louis, Mo.), which comprises a mixture of protease inhibitors with broad specificity for the inhibition of serine, cystein, aspartic and metallo-proteases, including 4-(2-aminoethyl)benzenesulfonyl fluoride (AEBSF), pepstatinA, E-64 and 1,10-phenanthroline. Of course, one of skill in the art will be able to prepare a protease inhibitor cocktail comprising the desired protease inhibitors.

As used herein, "EDTA" refers to ethylenediaminetetraacetic acid, having the structure depicted below:

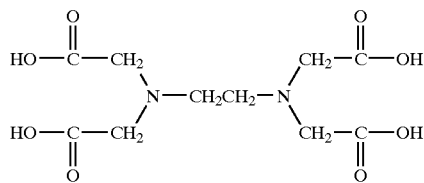

As used herein, an "extraction buffer" (or a "lysis buffer") is used in reference to a solution used during the disruption of cells (for example, disruption of cells so that a protein may be isolated). In some embodiments, an extraction buffer further comprises a detergent. In some embodiments, an extraction buffer comprises a protease inhibitor cocktail.

As used herein, "treating an extract under conditions such that a protein is isolated" refers to the biochemical steps carried out after cells have been lysed in the presence of an extraction buffer. In some embodiments, said treating may comprise precipitation of various components. In some embodiments, said treating may comprise centrifugation (for example to clarify the extract). In some embodiments, said treating may comprise column chromatography.

As used herein, "lectin" refers to any of a group of proteins that are not antibodies and do not originate in an immune system and which specifically bind carbohydrate-containing molecules, for example receptors on cell surfaces. Different lectins have different carbohydrate-binding specificities.

As used herein, "MOA" refers to the *M. oreades* lectin (i.e. agglutinin) which has binding specificity for the blood type B disaccharide, Ga1+1,3Ga1. Intact MOA purified from *M. oreades* comprises a single polypeptide of approximately 33 kDa, which may exist as a homodimer in native form.

As used herein, "chromatography" refers to process in which a mixture of molecules (e.g. a complex mixture as might be found in a cell extract) carried by a liquid is separated into components as a result of differential distribution of the different molecules as the flow around or over a stationary liquid or solid phase.

As used herein, "affinity chromatography" refers to chromatography (i.e. a subset of column chromatography) in which a macromolecule (for example, a glycoprotein) is isolated and purified by passing it in solution through a column that has been treated with a substance which will bind the macromolecule, such that the macromolecule is retained on the column. By way of non-limiting example, MOA-affinity chromatography comprises an affinity column comprising MOA immobilized to the solid phase of the column.

As used herein, "immobilized MOA" refers to MOA which is comprised on some form of solid support. While it is not intended that the nature of the solid support be limiting, a variety of solid supports are contemplated, including but not limited to Sepharose beads.

As used herein, an "immobilized-MOA affinity column" refers to an affinity column in which the solid matrix comprises immobilized MOA.

As used herein, contacting a sample with an immobilized MOA affinity column under conditions such that a glycoconjugate can bind is intended to refer to the steps that are carried out to allow specific binding of a glycoconjugate recognized by MOA to an MOA affinity column. For example, one of skill in the art will appreciate that factors such as buffer composition and flow rate can be adjusted to promote specific binding between a glycoconjugate comprised in the sample to the MOA affinity column. Once specifically bound, the glycoconjugate (comprising a saccharide) and MOA form a complex. Treating said complex under conditions such that the glycoconjugate is eluted from the column is intended to refer to the steps carried out to promote elution (i.e. release from the complex and column) of the glycoconjugate. One of skill in the art will appreciate that elution buffer composition will influence the binding between MOA and the glycoconjugate.

As used herein, "column chromatography" refers to chromatography in which the substances to be separated are introduced onto the top of a column packed with an affinity resin or adsorbent (e.g. silica gel, diatomaceous earth, alumina), pass through the column at different rates that depend on the affinity of each substance for the adsorbent and for the solvent or solvent mixture, and are usually collected in solution as they pass from the column at different times.

As used herein, "isothermal titration calorimetry" refers to a process for measuring binding affinity between two molecules, wherein the heat evolved even when small aliquots of a solution if the carbohydrate ligand is added isothermally to a solution of the lectin in a stirred, thermally-isolated cell is recorded. Additions are continued until the lectin binding sites are saturated and no further heat is evolved. This procedure is carried out on a commercially-available instrument, including but not limited to the CSC 4200 microcalorimeter (Calorimetric Sciences, Inc., Spanish Fork, Utah, USA). Data are analyzed using software supplied with the instrument, giving the binding constant, Ka. In situations where Ka and the concentration of lectin are sufficiently high, the stoichiometry of binding, and the molar enthalpy of binding ($\Delta H$) are also determined with reasonable certainty.

As used herein, "agglutination" refers to a reaction in which particles (such as red blood cells or bacteria) suspended in a liquid collect into groups or clumps. "Blood cell agglutination" refers to agglutination of red blood cells. In some embodiments, MOA binding to glycoconjugates on blood cell surfaces promotes their agglutination.

As used herein, "carbohydrate precipitation" refers to a reaction in which carbohydrate-containing molecules suspended in a liquid come out of solution and from a solid or particulate precipitate. In some embodiments, MOA binding to carbohydrate-containing molecules promotes their precipitation.

As used herein, "melibiose" refers to a disaccharide sugar $C_{12}H_{22}O_{11}$ formed by partial hydrolysis of raffinose.

As used herein, "Sepharose" refers to the Amersham Bioscience trademark name for any of a group of products based on bead-formed agarose gel. Agarose is a generic term referring to part of the complex mixture of charged and neutral polysaccharides known as agar. The agarose used to make Sepharose is obtained by a purification process that removes charged polysaccharides to give a gel with only a very small number of residual charged groups. Sepharose 4B has a bead diameter of between 40 and 165 μm. The structure of Sepharose 4B is depicted below:

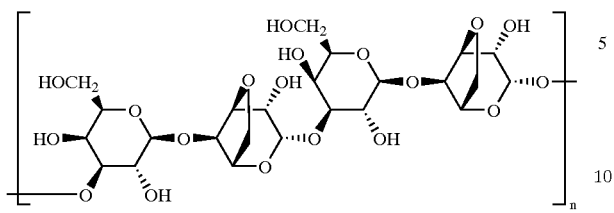

As used herein, "glycoconjugate" refers to any of a group of compounds (e.g. glycoproteins) consisting of sugars linked to e.g. proteins or lipids.

As used herein, "contacting a sample with labeled MOA under conditions such that a glycoconjugate is detected" is intended to comprise the incubation, washing and detecting steps carried out to detect a glycoconjugate in a sample which is specifically bound by MOA. By way of non-limiting example, binding of labeled MOA to the Galili epitope in porcine tissue may be detected by incubating the labeled MOA with a porcine tissue section, washing the section and carrying out analysis to detect any bound labeled MOA. As another non-limiting example, labeled MOA may be incubated with a Plasmodium-infected blood smear for a suitable incubation period, the smear is then washed, and bound labeled MOA is detected using appropriate means (which, as will be understood by one of skill in the art, will depend on the nature of the label).

As used herein, a "sample" refers to a biological specimen obtained from a subject. Samples include, but are not limited to, blood samples (including serum), tissue samples, saliva samples, sweat and urine samples.

As used herein, "symptoms of malaria" refer to any of the following: fever, which often appears in a characteristic pattern (e.g. with a 48 hr or 72 hr periodicity), fever preceded by a feeling of intense cold, headache, muscle pains and vomiting.

As used herein, "*Plasmodium falciparum* merozoites" refers to a specific life cycle stage of the *Plasmodium falciparum* protozoa.

As used herein, "Galα1,1,3Gal" refers to the disaccharide having the structure shown below

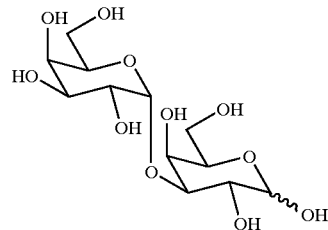

As used herein, "Galα1,3Gal" refers to the trisaccharide having the structure shown below;

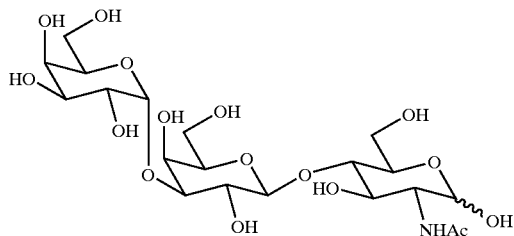

As used herein, "Glα1,3 [L-Fucα1,2]Gal" refers to the trisaccharide having the structure shown below:

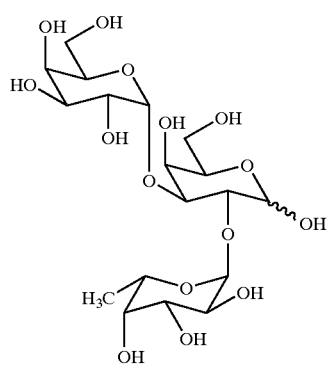

As used herein, "L-Fucα1,2Galβ1,4Gal" refers to the trisaccharide having the structure shown below:

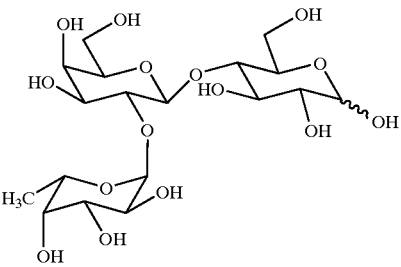

As used herein, "antibiotic induced diarrhea" or "antibiotic associated diarrhea" refers to diarrhea that occurs concurrent with or just after a course of antibiotic treatment. The diarrhea results due to the disruption in the normal bowel flora by the antibiotic, and the resulting overgrowth of some types of bacteria, including *C. difficile*. *C. difficile* produces at least two toxins (one of which is known as Toxin A), which damage the bowel wall and trigger the diarrhea. Symptoms of antibiotic associated diarrhea include at least one of the following, occurring during a course of antibiotic treatment: mild diarrhea, watery and foul-smelling diarrhea, crampy abdominal pain, abdominal tenderness, fever, and pus or blood in the diarrhea. Depending on the severity of the diarrhea, symptoms of dehydration may also be present, including a very dry mouth, intense thirst, decreased urination and extreme weakness.

As used herein, "overnight" refers to a period of approximately 12 hours, but may be between approximately 8 and approximately 24 hours.

As used herein, "room temperature" refers to a temperature in the range of 15° C. to 25° C.

As used herein, the term "nucleic acid hybridization analysis" refers to methods using hybridization of nucleic acids (e.g. DNA and RNA) to each other, i.e. the formation of base paired duplexes between nucleic acids. The duplexes may be completely complementary, or the duplexes may contain mismatched bases. The present invention contemplates the use of methods, including but not limited to Southern analysis, Northern analysis, reverse transcriptase polymerase chain reaction (RT-PCR), in situ RT-PCR, differential display, and in situ hybridization, including but not limited to fluorescence in situ hybridization (FISH).

As used herein, the term "subject" refers to both humans and animals.

As used herein, the term "patient" refers to a human subject whose care is under the supervision of a physician or who has been institutionalized (e.g. in a hospital).

As used herein, the term "gene" refers to a DNA sequence that comprises control and coding sequences necessary for the production of a polypeptide or protein precursor. The polypeptide can be encoded by a full-length coding sequence, or by a portion of the coding sequence, as long as the desired protein activity is retained.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in a specific sequence (i.e. a linear order of nucleotides). A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two bases to about one hundred bases. The word "oligo" is sometimes used in place of the word "oligonucleotide".

Nucleic acid molecules are said to have a "5' terminus" (5' end) and a "3'terminus" (3' end) because nucleic acid phosphodiester linkages occur to the 5' carbon and 3' carbon of the pentose ring of the substituent mononucleotides. The end of a nucleic acid at which a new linkage would be to a 5' pentose carbon is its 5' terminal nucleotide. The end of a nucleic acid at which a new linkage would be to a 3' pentose carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring, and as the "3' end" if its 3' oxygen is not linked to a 5' phosphate of a subsequent mononucleotide pentose ring.

With respect to nucleic acid sequences, one of skill in the art will appreciate that polymorphisms are often found in populations (see below), and any such polymorphisms contained within any of the sequences of interest (for example, the cDNA sequence encoding MOA) are also within the scope of the present invention.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

For some variants (i.e. modified or mutant forms of a gene), there is no selection against individuals carrying the variant form, and so both forms (wild-type and modified) may be relatively common in the general population. This is referred to as "genetic polymorphism", which is defined herein as a genetic variation in which the frequency of two or more forms, or alleles, is at least 1% in the population. Polymorphisms within the MOA nucleic acid sequence are specifically contemplated.

As used herein in reference to a nucleic acid sequence (for example a cDNA or genomic sequence), the term "portion" (as in "a portion of a cDNA sequence") refers to fragments of that nucleic acid sequence. The fragments may range in size from five nucleotides to the entire nucleic acid sequence minus one nucleotide.

The term "antisense" as used herein refers to a deoxyribonucleotide sequence whose sequence of deoxyribonucleotide residues is in reverse 5' to 3' orientation in relation to the sequence of deoxyribonucleotide residues in a sense strand of a DNA duplex. Antisense also refers to the "reverse complement orientation". By way of example, the reverse complement of the nucleotide sequence 5'-GATCC-3' is 5'-CTAGG-3'. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

As used herein, the term "overexpression" refers to the production of a gene product in transgenic organisms or in diseased tissue or in patients or subjects with a disease that exceeds levels of production in normal or non-transformed organisms or in non-diseased tissues or individuals.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

As used herein the term "coding region" when used in reference to a structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the terms "complementary" or "complementarity" when used in reference to polynucleotides refer to polynucleotides which are related by the base-pairing rules. For example, the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods (such as nucleic acid hybridization methods) which depend upon binding between nucleic acids.

A "complement" of a nucleic acid sequence as used herein refers to a nucleotide sequence whose nucleic acids show total complementarity to the nucleic acids of the nucleic acid sequence.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 mg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 mg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

Thus, the art understands that different applications may require different levels of stringency, and one of skill in the art can determine the appropriate stringency for a given hybridization. In some embodiments, "contacting a sample with an isolated nucleic acid" involves hybridization under high stringency conditions, such that a nucleic acid sequence in the sample is detected.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

As used herein, "derivatives" of proteins of interest (e.g. the MOA protein) can refer to a number of alterations in such proteins. In some embodiments, the derivatives comprise proteins with amino acid sequence changes. Such changes can be conservative amino acid substitutions, amino acid deletions or amino acid insertions, provided that the activity of the protein is retained. Preferably, the alterations are conservative amino acid changes.

For example, it is contemplated that an isolated replacement of a leucine with an isoleucine or valine, an alanine with a glycine, a threonine with a serine or a similar replacement of an amino acid with a structurally related amino acid (i.e. conservative substitutions) will not have a major effect on the biological activity of the resulting molecule. Conservative substitutions are those that take place within a family of amino acids that are related by their side chains. Amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In an alternative, yet similar fashion, the amino acid repertoire can be grouped as: (1) acidic (aspartate, glutamate); (2) basic (lysine, arginine, histidine); (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (See e.g. Stryer ed., Biochemistry, 2E, W H Freeman and Co. (1981) pp. 13–16).

Thus, in certain embodiments, modifications of the MOA protein sequence are contemplated by the present invention. Guidance in determining which and how many amino acid residues may be substituted, inserted, or deleted without abolishing biological activity may be found by using computer programs well known in the art, for example, DNAStar software or GCG (Univ. of Wisconsin).

As used herein in reference to an amino acid sequence or a protein, the term "portion" (as in "a portion of an amino acid sequence") refers to fragments of that protein. The fragments may range in size from a minimum of four amino acid residues to the entire amino acid sequence minus one amino acid.

As used herein, the term "fusion protein" refers to a chimeric protein containing the protein of interest (e.g., MOA or portions thereof) joined to an exogenous protein fragment (e.g., the fusion partner). The fusion partner may enhance the solubility of the protein of interest as expressed in a host cell, may provide an affinity tag to allow purification of the recombinant fusion protein from the host cell or culture supernatant, or both. In other embodiments, the nucleic acid sequences encoding the fusion proteins are contemplated.

The term "isolated" when used in relation to a nucleic acid, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence.

As used herein, the terms "vector" and "vehicle" are used interchangeably in reference to nucleic acid molecules that transfer DNA segment(s) from one cell to another. Vectors may include plasmids, bacteriophages, viruses, cosmids, and the like.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" and "targeting construct" refer to nucleic acid sequences comprising a sequence of interest flanked on either side by recognition sequences that are capable of homologous recombination with cognate sequences in the genome in such a way that the sequence of interest replaces any DNA sequences that are located between the cognate sequences in the genome. The flanking recognition sequences can consist of recognition sites for restriction enzymes or site specific recombinases such as Flp or Cre, exogenous genes including but not limited to those that encode thymidine kinase or confer resistance to antibiotics such as neomycin and hygromycin, marker genes such as LacZ and eGFP, as well as portions of the targeted gene itself or sequences from other genes of interest.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. The present invention contemplates the gene encoding MOA in operable combination with a promoter.

The term "selectable marker" as used herein, refers to a gene which encodes an enzyme having an activity that confers resistance to an antibiotic or drug upon the cell in which the selectable marker is expressed. Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

Transcriptional control signals in eukaryotes comprise "promoter" and "enhancer" elements. Promoters and enhancers consist of short arrays of DNA sequences that interact specifically with cellular proteins involved in transcription (Maniatis, et al., *Science* 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy. Alternatively, mRNA localization can be determined by in situ hybridization.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed and placed in operable combination with a second gene, thereby making it a "heterologous" promoter in operable combination with said second gene. A variety of such combinations are contemplated (e.g. the first and second genes can be from the same species, or from different species).

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning. A Laboratory Manual*, 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/Bc/I restriction fragment and directs both termination and polyadenylation (Sambrook, supra, at 16.6–16.7).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. When introducing foreign DNA into yeast cells, the term "transformation" is commonly used.

The term "transgenic" when used in reference to a cell refers to a cell which contains a transgene, or whose genome has been altered by the introduction of a transgene. The term "transgenic" when used in reference to a tissue or to an organism, such as a mouse, refers to a tissue or organism, respectively, which comprises one or more cells that contain a transgene, or whose genome has been altered by the introduction of a transgene. Transgenic cells, tissues and organisms may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., P-glucuronidase) encoded by the transgene. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "amplification" is defined as the production of additional copies of a nucleic acid sequence and is generally carried out using polymerase chain reaction technologies well known in the art (Dieffenbach and GS Dvekler, PCR *Primer, a Laboratory Manual*, Cold Spring Harbor Press, Plainview N.Y. [1995]). As used herein, the term "polymerase chain reaction" ("PCR") refers to the methods disclosed in U.S. Pat. Nos. 4,683,195, 4,683,202 and 4,965,188, all of which are incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled or biotinylated deoxyribonucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc. Reverse transcription PCR (RT-PCR) refers to amplification of RNA (preferably mRNA) to generate amplified DNA molecules (i.e. cDNA). RT-PCR may be used to quantitate mRNA levels in a sample, and to detect the presence of a given mRNA in a sample. PT-PCR may be carried out "in situ", wherein the amplification reaction amplifies mRNA for example, present in a tissue section.

As used herein, the term "sample template" refers to a nucleic acid originating from a sample which is analyzed for the presence of "target". In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other that those to be detected may be present as background in a test sample.

A; used herein, the term "primer" refers to an oligonucleotide, whether occurring naturally (e.g., as in a purified restriction digest) or produced synthetically, which is capable of acting as a point of initiation of nucleic acid synthesis when placed under conditions in which synthesis of a primer extension product which is complementary to a nucleic acid strand is induced (i.e., in the presence of nucleotides, an inducing agent such as DNA polymerase, and under suitable conditions of temperature and pH1). The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method.

As used herein, the term "probe" refers to a polynucleotide sequence (for example an oligonucleotide), whether occurring naturally (e.g., as in a purified restriction digest) or produced synthetically, recombinantly or by PCR amplification, which is capable of hybridizing to another nucleic acid sequence of interest. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used here n interchangeably. In addition to probes, primers and deoxynucleoside triphosphates may contain labels; these labels may comprise, but are not limited to, $^{32}$P, $^{33}$P, $^{35}$S, enzymes, fluorescent molecules (e.g., fluorescent dyes) or biotin.

As used herein, "FISH" refers to fluorescence in situ hybridization, a technique in which labeled DNA probes (which can be prepared, for example, from cDNA sequences or genomic sequences contained in cosmids or bacterial artificial chromosomes [BACs]) are hybridized to cytogenetic or histological specimens. Such specimen include, but are not limited to metaphase chromosome spreads and interphase nuclei prepared from tissue or blood specimens, and formaldehyde-fixed, paraffin-embedded tissue sections. Tissue sections prepared from fresh frozen tissue can also be used. Fluorescent labels can be directly incorporated into the probe, or can be applied as antibody-label conjugates which bind to affinity labels (e.g. biotin or digoxigerin) incorporated into the probe, either directly, or as an antibody "sandwich" (i.e. a primary and a secondary antibody). The fluorescent dyes include, but are not limited to, rhodamine, texas red, FITC (fluorescein isothiocyanate) and TRITC (tetramethyl rhodamine isothiocyanate). The fluorescent labels are detected using a fluorescence ice microscope equipped with a mercury or xenon lamp (as an illumination source) and appropriate filters for excitation and emission.

DESCRIPTION OF THE INVENTION

In several embodiments, the present invention contemplates a purified lectin, MOA, with specificity for Gal$\alpha$1, 3Gal-containing epitopes. In some embodiments, the MOA is purified from the fairy-ring mushroom *Marasmius oreades*. In some embodiments, MOA is expressed recombinantly, for example in bacteria. In some embodiments, the nucleic acid sequence encoding MOA is contemplated. In other embodiments, MOA is contemplated for use in a variety of applications, including but not limited to affinity purification, diagnostics, and therapeutics, including, for example, use in the field of xenotransplantation. The description that follows is divided into the following sections: I. Overview of the Purification of MOA, II. Binding Specificity of MOA, III. Cloning and Recombinant Expression of MOA, IV. Methods of Using MOA and IV. Therapeutic Formulations.

I. Overview of the Purification of MOA

In some embodiments, MOA is purified from *M. oreades* mushrooms. The mushroom may be harvested from outdoor plots, or may be ordered from commercial or gourmet food sources, for example from American Mushroom Hunter Corp. (Middle Town, NJ). Fresh mushroom tissue is homogenized and then strained and centrifuge (see Examples below). A series of chromatographic affinity columns is then used to purify the MOA lectin. In initial experiments, carried out in the presence of phenylmethylsulfonyl fluoride (PMSF), three peptides were detected by SDS-PAGE mass spectrometric analysis: one with a Mr of 33 KDa, one with a Mr of 23 kDa and one with a Mr of 10 kDa. A lectin from *M. oreades* having subunits of 33 kDa and 23 kDa was reported previously [Horejsl et al. *Biochim. Biophys. Acta* 538:299 (1978)].

Subsequent analysis (see Examples below), including analysis of tryptic fragments, isolation in the presence of EDTA and recombinant expression showed that the intact MOA lectin is a single peptide of approximately 33 kDa. While not to be limited to any particular mechanism, and with the understanding that knowledge of the underlying mechanism is not required for the practice of the present invention, it is believed that the originally identified 23 kDa and 10 kDa peptides are formed by metalloprotease cleavage of the intact, 33 kDa peptide.

In the presently preferred embodiments for isolation of MOA from mushrooms (see Example 2 below), the extraction procedure is carried out (i) in the presence of a protease inhibitor cocktail (including but not limited to product P8215, from Sigma), rather than the PMSF (i.e. the protease inhibitor cocktail replaces the PMSF), (ii) $Ca^{2+}$ is eliminated, (iii) EDTA is included in all buffers and (iv) the extraction and initial ammonium sulfate precipitations are carried out under an atmosphere of argon. Again, while to be limited to any particular mechanism, it is believed that these conditions reduce or eliminate proteolysis and possibly oxidation of the MOA lectin.

Based on results of size exclusion chromatography (see Examples below) carried out using native MOA lectin isolated using the preferred methods (which include use of a protease inhibitor cocktail, the elimination of $Ca^{2+}$, the presence of EDTA and an atmosphere of argon for the initial extraction and precipitation steps) it is believed that native MOA exists as a homodimer of the 33 kDa polypeptide.

In some embodiments, a composition comprising an isolated MOA polypeptide of approximately 33 kDa is contemplated, wherein said composition is substantially free of polypeptides of approximately 23 kDa and approximately 10 kDa (ie. fragment, of the 33 kDa polypeptide). In some embodiments, it is contemplated that said composition will have undetectable levels of 23 kDa and 10 kDa polypeptides, as detected by Coomassie blue staining of SDS-PAGE gels (i.e. said composition is substantially free of polypeptides of 23 kDa and 10 kDa). While other detection is methods (e.g. silver staining of SDS-PAGE gels) may detect small amounts of 23 kDa and 10 kda polypeptides, the inability to visually detect these polypeptides by Coomassie Blue staining of a purified MOA preparation is sufficient to classify such preparations as "substantially free" of the 23 kDa and 10 kDa polypeptides. In some embodiments, said composition is prepared from *Marasmius oreades* mushrooms. In some embodiments, said composition comprising said isolated MOA polypeptide, wherein said polypeptide is substantially free of polypeptides of 23 kDa and 10 kDa is contemplated as being used in a variety of applications, including but not limited to affinity purification, xenotransplantation, and diagnostics (e.g. detection of the presence of *Plasmodium falciparum* merozoites in a blood sample).

II. Binding Specificity of the MOA Lectin

While the MOA used in various individual experiments (see Examples below) may have been either isolated from *M. oreades* (as described supra), or produced recombinantly (see below), it should be noted that the binding specificity of the lectin is the same, regardless of the source (i.e. recombinant or biochemically isolated). As noted above, in instances where the lectin is biochemically isolated from *M. oreades*, the preferred isolation procedure is carried out in $Ca^{2+}$-free buffers, in the presence of a protease inhibitor cocktail and EDTA, and (for certain steps) under an argon atmosphere.

A. Blood Group Specificity

In some embodiments, blood group specificity of MOA is determined in hemagglutination assays (see Examples below). Briefly, formaldehyde-treated erythrocytes in V-well microtitre plates are used in a protocol as described in Mo et al. [*J. Biol. Chem* 275:10623 (2000)], herein incorporated by reference. Strong hemagglutination activity was detected for human blood group B (human B erythrocytes), but very little activity was detected for human type A or type O erythrocytes. Example 3, below, presents the data for agglutination activity against a variety of cell types. MOA readily agglutinated Ehrlich ascites tumor cells, which contain the same Galα1,3Gal di- and Galα1,3Galβ1,4Gal trisaccharides in their cell membrane [Eckhardt and Goldstein. *Biochemistry* 22: 5290 (1983)].

In other embodiments, blood group specificity of MOA is determined by quantitative precipitation assays. Quantitative microprecipitation assays with soluble cyst blood group substances and inhibition of precipitation by sugar haptens were performed as described in Mo et al., [*J. Biol. Chem.* 275:10623 (2000)]. As shown in Example 4 below, MOA reacts strongly with human blood type B substance, not at all with type A substance, and rather weakly with type H substance.

B. Sugar Ligand Binding

Sugar ligand binding to MOA was conducted using three approaches: (i) inhibition of Type B hemagglutination, (ii) hapten inhibition of MOA-type B substance precipitation and (iii) isothermal calorimetry (see examples below). All three methods gave approximately the same results, with the calorimetric data being the most precise.

Being a blood type B agglutinin, MOA was assayed primarily against D-galactosyl-terminated sugars and oligosaccharides. As shown in the examples below, lactose, N-acetyllactosamine and melibiose (Galα1,6Glc) were very poor ligands. Methyl α-galactopyranoside was similarly very poor. The blood group B disaccharide, Galα1,3Gal, was an excellent ligand with Ka $6.0\times10^3$ $M^{-1}$ whereas the isomeric disaccharides Galα1,2Gal, Glα1,4Gal and Galα1,6Gal bound poorly or not at all. Addition of a GlcNAc group to the reducing end of Galα1,3Gal to give Galα1,3Galβ1,4GlcNAc increased the binding by approximately 50% to Ka $9.7\times10^3$ $M^{-1}$. Similarly, adding an L-fucosyl group to the disaccharide to afford the blood group B branched trisaccharide (Galα1,3[L-Fucα1,2]Gal) enhanced its affinity to MOA 4-fold (Ka $3.6\times10^4$ $M^{-1}$). Finally, the trisaccharide L-Fucα1,2Galβ1,4Glc (fucosyllactose), related to the blood group H trisaccharide, had a Ka of 548 $M^{-1}$ by isothermal titration calorimetry. It appears that the L-fucosyl residue makes a significant contribution to the binding affinity of the essentially inactive lactose (Ka=185 $M^{-1}$). While not limited to any particular mechanism, and with the understanding that knowledge of the underlying mechanism is not required for the practice of the invention, it is believed that recognition of the L-fucosyl moiety is the reason for limited agglutination of human O erythrocytes and a weak precipitin curve with blood group H substance.

Other precipitation reactions were carried out (see Examples below) and it was found that MOA reacts strongly with laminin (which has been shown to contain Galα1, 3Galβ1,4GlcNAc-end groups [Shibata et al. *FEBS Letter* 214:194 (1982); Knibbs et al. *Biochemistry* 28:6379 (1989)]. MOA also reacted strongly with bovine thyroglobulin, which has been shown to have the same determinants [Spiro and Bhoyroo *J. Biol. Chem.* 259:9858 (1984)]. No precipitin reaction was observed with pigeon ovalbumin, which is known to contain multiple Glα1,4Gal end groups [Suzuki et al. *J. BioL. Chem.* 276: 23230 (2001)], thus demonstrating the specificity of MOA for Galα 1,3Gal groups. MOA also failed to recognize the blood group type A disaccharide (GalNAcα1,3Gal), as no precipitation was observed with this disaccharide-polyacrylamide glycoconjugate.

Binding assays with labeled MOA are also contemplated. It is not intended that the nature of the label be limiting. A variety of labels are contemplated, including but not limited to radioactive labels (e.g. $^{35}$S, $^{14}$C, $^{125}$I, $^3$H and $^{131}$I), fluorescent labels (e.g. rare earth chelates (europium chelates) or fluorescein and its derivatives, rhodamine and its derivatives, dansyl, Lissamine, phycoerythrin and Texas Red), and various enzyme-substrate labels (see e.g. U.S. Pat. No. 4,275,149, herein incorporated by reference, and leciferase, luciferin, 2,3-dihydrophthalazinediones, malate dehydrogenase, urease, peroxidase such as horseradish peroxidase (HRP), alkaline phosphatasae (AP), β-galactosidase, glucomaylase, lysozyme, sacharide oxidases (e.g. glucose oxidase, galactose oxidase and glucose-6-phosphate dehydrogenase), heterocyclic oxidases (such as uricase and xanthine oxidase), lactoperoxidase, microperoxidase and the like). Biotin is also contemplated as a label. In one embodiment, fluorescein-labeled MOA is contemplated for use in binding assays. In one embodiment, fluorescein-labeled MOA is used to stain porcine striated skeletal muscle (see, Example 7 below). Endothelial cells lining the capillaries are the significant structures stained by the lectin. In another embodiment, fluorescein-labeled MOA is used to stain *Plasmodium falciparum* merozoites in a human blood smear (see Example 7 below).

Further insight into the carbohydrate specificity of MOA was obtained by using immobilized MOA. Immobilization of MOA on a variety of supports is contemplated. In one embodiment, MOA is immobilized on a matrix that can be used in an affinity column (see below). In some embodiments, the matrix comprises Sepharose 4B beads. In some Embodiments, the MOA-conjugated Sepharose 4B beads are packed in a column for binding and affinity isolation and purification studies. Briefly, the MOA-Sepharose column is loaded with glycan, glycoconjugate or serum sample to be tested, then washed with an appropriate buffer (including but not limited to PBS). Bound components are eluted with a suitable elution buffer (including but not limited to 1,3-diaminopropane in NaCl), and the collected fractions are analyzed for the presence of protein or glycan (see Example 6 below). The fractions containing the bound components (eluted as described herein) can be pooled and concentrated.

In order to confirm the binding specificity of the MOA lectin, various glycans and glycoconjugates were applied to the MOA-Sepharose column. Laminin purified from the EHS sarcoma and bovine thyroglobulin (both of which contain multiple Galα1,3Galβ1,4GlcNAc end groups [Knibbs et al. *Biochemistry* 28: 6379 (1989); Spiro and Bhoyroo. *J. Biol. Chem.* 259:9858 (1984)] bound tightly to the immobilized MOA (see Example below). Asialofetuin and degalactosylated bovine thyroglobulin passed through the column, not being recognized by MOA. Pigeon ovalbumin (which contains Galα1,4Gal-terminated N-glycans [Suzuki et al. *J. Biol. Chem* 276: 23221 (2001)] also did not bind the MOA-Sepharose column. Blood group H substance, which has terminal Fucα1,2Galβ1,4GlcNAc chains, also failed to bind MOA-Sepharose, although the trisaccharide Fucα1,2Gal=1,4Glc exhibited low but measurable binding in solution (see above). Galactomannan, which has Galα1,6Man branches on a linear Manβ1,4Manβ backbone also failed to bind immobilized MOA. While not to be limited to any particular mechanism, and with the understanding that knowledge of the underlying mechanism is not required for the practice of the invention, it is believed that MOA exhibits trisaccharide specificity and requires a Galα1,3Gal linkage for binding. Interactions of the Sepharose-immobilized MOA with other substances are described below.

III. Cloning and Expression of Recombinant MOA

The present invention contemplates the recombinant expression of MOA and the resulting composition, the only known Galα1,3Gal specific lectin. This is also the first reported protein sequence from the fairy-ring mushroom *Marasmius oreades*. MOA appears to belong to the ricin protein superfamily because of the presence of a conserved carbohydrate binding domain originally identified in the B chain of ricin, one of the first studied hemagglutinins. Many of these proteins, like the ricin B chain itself, promote the internalization of disulfide-linked toxic protomers through their binding to glycosylated cell surface receptors. There is no evidence that MOA functions in this manner.

Structural analysis of ricin domains suggests that they are composed of three repeating subdomains that may have originated from an ancestral galactose-binding motif. Closer analysis of the three subdomains of MOA indicates strong conservation with the key residues in the 1α and 2γ subdomains of ricin and ebulin (FIG. 4). Structural determination of these proteins in the presence of sugar shows binding to these two subdomains. All of the MOA subdomains have the conserved QXW motif. In ricin the conserved tryptophan is necessary for hydrophobic packing of the core structure, while the glutamine coordinates the conserved aspartic acid that hydrogen bonds with the third and fourth oxygens of the galactosyl moiety. The asparagine prior to the QXW motif also hydrogen bonds with the O3 and O4 of the sugar. The corresponding histidine found in the MOA subdomains could function similarly. Additionally, there is a conserved hydrophobic position, occupied by tryptophan, tyrosine, or phenylalanine between the conserved aspartic acid and asparagine. This residue forms a stacking interaction with the sugar ring. In the MOA subdomains this position is occupied by a conserved tryptophan.

Because the essential features required for galactosyl binding are conserved in MOA, it is interesting that the specificity of ricin is very different from that of MOA. While MOA is specific for Galα1,3Gal-containing sugars, ricin binds well with β-1,3 or β-1,4-linked galactose-terminated sugars. Like MOA, ricin shows higher affinity for larger, more complex saccharides than for simple sugars. The affinity constant for lactose binding to ricin is 10-fold greater than for galactose alone. Similarly, MOA binds Galα1,3Gal with an affinity constant 44-fold greater than that for Meα-Gal. While the structure of ricin shows hydrogen bonding exclusively to the terminal sugar, it is clear that elements outside of the main binding pocket are important for determining the strength and specificity of binding.

Of particular interest in explaining the difference between MOA and other ricin domain proteins could be the loop region between the stacking hydrophobic and sugar binding asparagine/histidine. Unlike other subdomain segments, it does not model well onto ricin. This loop is longer in MOA than in ebulin and ricin by one to three residues, and appears structurally different with the absence of a conserved proline followings the hydrophobic stacking residue. While the present invention is not limited to any particular mechanism, this region could provide an additional hydrogen bonding interface specific for Galα1,3Gal containing sugars either through direct side-chain contact or water-mediated interactions and would be appropriately positioned to sterically block sugars not in the 1,3 orientation.

The cloning and expression of the recombinant MOA provides a route for understanding the structure and unique carbohydrate binding specificity of this novel lectin. Crystallographic structure determination of MOA in the presence of bound sugar should provide the explanation for the specific binding of G1α1,3Ga1.

In order to clone the MOA cDNA (see Example 8 below), MOA was digested with trypsin and endoproteinase Asp-N and the peptide fragments were purified by high performance liquid chromatography. Amino acid sequence data were obtained for eight peptides. Using oligonucleotide sequences prepared based on the peptide sequences, RT-PCR was carried out on mRNA isolated from *M. oreades* and a 41 base pair cDNA fragment was obtained. The full-length cDNA was obtained using 5' and 3' rapid amplification of cDNA ends (RACE). MOA cDNA encodes a protein of 293 amino acids that contains a ricin domain. Recombinantly expressed and purified MOA retains the specificity and affinity observed with the native protein.

In one embodiment, the cDNA sequence encoding MOA [SEQ ID NO: 1] is contemplated. In one embodiment, a polymorphism in SEQ ID NO: 1 is specifically contemplated. In one embodiment, the amino acid sequence encoded by SEQ ID NO: 1 is contemplated (i.e. the MOA amino acid sequence; SEQ ID NO: 2; FIG. 1A). In one embodiment, a polymorphism in SEQ ID NO: 2 is specifically contemplated. In one embodiment, the polymorphism comprises an asparagine at position 200, rather than an aspartic acid. The polymorphic sequence comprising asparagine at position 200 [SEQ ID: NO: 3] is presented in FIG. 2. While not limited to any particular mechanism, it is believed that this polymorphism is unlikely to alter binding specificity as it lies outside the predicted ricin domain.

Ir some embodiments, a purified nucleic acid having the sequence of SEQ ID NO: 1, or portions thereof is contemplated. In some embodiments, a purified nucleic acid sequence having a sequence polymorphism in SEQ ID NO: 1 is contemplated. Said polymorphism may comprise between one and four nucleotide differences in comparison to SEQ ID NO: 1. In some embodiments, an isolated nucleic acid having the sequence of SEQ ID NO: 1, or portions thereof is contemplated for use as a probe or primer (for example, for use in hybridization or amplification applications). In some embodiments, an isolated nucleic acid sequence having a sequence that is the complement of SEQ ID NO: 1 is contemplated. In some embodiments, said complementary sequence, or portions thereof, is contemplated for use as a probe or primer (for example, for use in hybridization or amplification reactions). In some embodiments, said probe or primer sequences are labeled. In some embodiments, said label comprises a radioactive label (including but not limited to $^{32}P$, $^{33}P$ and $^{35}S$), while in other embodiments, said label comprises biotin. In other embodiments, said label comprise; a fluorescent moiety, including but not limited to fluorescein, Texas Red and rhodamine. In some embodiments, said hybridization reactions comprise Northern analysis. In some embodiments, said amplification reactions comprise PCR and RT-PCR.

In some embodiments, a vector comprising SEQ ID NO: 1 or portions thereof is contemplated. In some embodiments, said vector is an expression vector. In some embodiments, said expression vector comprises (in operable combination) an inducible promoter including but not limited to an IPTG-inducible promoter, for expression of SEQ ID NO: 1 (i.e. said inducible promoter is operably linked to SEQ ID NO: 1). In some embodiments, said expression vector is introduced into a host cell. Thus, in some embodiments, a cell comprising an expression vector comprising SEQ ID NO: 1 is contemplated. In some embodiments, said host cell is selected from the group consisting, of a bacterial cell, a yeast cell, an insect cell and a mammalian cell. In some embodiments, said host cell expresses SEQ ID NO: 1 from said vector. Thus, in some embodiments, a host cell comprising recombinantly expressed MOA protein (e.g. SEQ ID NO: 2) is contemplated. In some embodiments, said recombinantly expressed MOA protein is purified from said host cell. In some embodiments, said purification comprises the steps of (a) providing a host cell expressing said recombinant MOA, (b) lysing said host cells to generate an extract; and (c) purifying said recombinant MOA from said extract. In some embodiments, said purification step (c) comprises column chromatography. In some embodiments, said host cell is a bacterial cell. In some embodiments, said expression of recombinant MOA in said host cell comprises expression from an expression vector comprising SEQ ID NO: 1.

In some embodiments, said recombinantly expressed MOA is purified. Host cells expressing recombinant MOA are lysed in the presence of an appropriate buffer (see Example below). The resulting extract is run through a French press and the insoluble fraction is removed by centrifugation. The soluble fraction is then adsorbed n a melibiose-Sepharose column followed by lactose elution, as described supra and in the Examples below for purification of MOA from *M. oreades* extracts.

IV. Uses of the MOA Lectin

It is not intended that the present invention be limited by the particular use of MOA. Binding of this novel lectin can be used for blood testing. This lectin is a Blood Group Type B agglutinin. It can be used in standard agglutination assays. On the other hand, the present invention contemplates using the labeled protein for cell binding.

In a preferred embodiment, binding can be done to mask an immunogenic epitope on a tissue for transplantation. More specifically, MOA recognizes the porcine xenotran plantation epitope with high affinity. The reactions to xenografted tissues include hyperacute rejection [the activation of the host complement system after binding of xenoreactive natural antibody (XNA), subsequent endothelial cell, platelet and coagulation system activations] and delayed xenograft rejection (cell-mediated adherence and activation mechanisms). Because MOA binds xenograft tissue epitopes, MOA may effectively block XNA binding and rejection. In one embodiment, porcine tissue to be transplanted is treated with MOA prior to transplantation. In another embodiment, porcine tissue is transplanted and the patient is administered MOA (or a portion thereof) to avoid rejection (e.g. intravenous administration, local administration, etc.)

In yet another embodiment, binding can be used to detect a microorganism (e.g. binding to *Plasmodium falciparum* merozoites) or a cancer cell. Finally, binding can be used to cause disease (e.g. administration of the protein to cause a kidney pathology).

In other embodiments, MOA is contemplated for use in the detection and preliminary characterization of glycoconjugates containing G1α1,3Ga1 di- and Ga1α1,3Ga1β1, 4G1cNAc tri-saccharides on cell surfaces and solution. These epitopes have been found, for example, in the basement membranes of mice, rats and rabbits, the surface of 3T3 cells, calf thyroid plasma membranes, and the plasma membranes of Ehrlich ascites tumor cells. As noted above, porcine tissues and organs contain the G1α1,3Ga1β1, 4G1cNAc epitope. By comparing the strength of binding of MOA to an unknown saccharide to known standards (including but not limited to G1α1,3Ga1, Ga1α1,3Ga1β1, 4Ga1Nac and Ga1α1,3[Fucα1,2]Ga1) one of skill in the art can make a preliminary determination of the structure of the unknown saccharide.

In an alternative embodiment, an immobilized form of MOA can be used for isolating glycoconjugates, polysaccharides and oligosaccharides. Methods for immobilizing lectins on a solid support are well known to the skilled artisan, and a representative conjugation of MOA to Sepharose B is presented in Example 6 below. Immobilized MOA can also be used for resolving mixtures of saccharides having G1α1,3Ga1 end groups. Methods of using immobilized MOA include the steps of contacting the immobilized MOA with a solution containing the saccharide of interest, incubating the solution and the immobilized MOA under conditions to permit binding of the saccharide to the MOA, washing the immobilized MOA-saccharide conjugate to remove all unbound compounds from the solution, and finally, eluting the saccharide from the immobilized MOA. The immobilized MOA can be used in a column and the solution run through the column, or the immobilized MOA can be added directly to the solution. The saccharide can be eluted from the immobilized MOA by contacting the MOA-saccharide conjugate with a solution containing, for example, G1α1,3Ga1. The saccharide of interest will then be released from the immobilized MOA due to competition from the disaccharide. Alternatively, the saccharide of interest can be eluted from the immobilized MOA by changing the pH of the eluting solution as compared to the pH of the washing solution. While not limited to any particular mechanism, it is believed that as the pH of the eluting solution becomes basic or acidic, MOA begins to denature, releasing the bound saccharide of interest.

In other embodiments, the immobilized MOA can be used in the affinity purification of serum components from human and animal serum. In one embodiment, serum samples from humans and a variety of animals can be applied to a column comprising Sepharose B-immobilized MOA. Following incubation and washing, bound serum components can be eluted. In one embodiment, $\alpha_2$-macroglobulin is eluted from serum from subjects with type B blood (see Example 6 below). Affinity isolation of $\alpha_2$-macroglobulin by immobilized MOA confirms the presence of blood group B epitopes on $\alpha_2$-macroglobulin from the serum of type B subjects.

In some embodiments, affinity isolation of other glycoconjugates is contemplated. In one embodiment, isolation of the *Plasmodium falciparum* merozoite glycoconjugate to which MOA binds is contemplated. Merozoites can be disrupted to produce an extract, using methods well known to one of skill in the art. For example, in one embodiment, merozoites can be disrupted by detergent, while in another embodiment, merozoites can be disrupted by sonication. It is not intended that the purification be limited to any particular mechanism of disruption. In some embodiments, the extract produced by disruption of the merozoites is subjected to centrifugation to remove insoluble material. The clarified supernatant comprising the merozoite glycoconjugate is then applied to a column comprising Sepharose B-conjugated MOA. Subsequent incubation, washing and elution steps are carried out as describe above and in the examples below. In some embodiments, the affinity isolated and purified *P. falciparum* merozoite glycoconjugate can be used in a variety of applications, including but not limited to vaccination against malaria (i.e. a composition comprising the affinity isolated and purified *P. falciparum* merozoite glycoconjugate can be administered to a subject under conditions such that protection against malaria is provided).

As one of skill in the art will appreciate, Sepharose B-immobilized MOA affinity columns can be used for the affinity isolation and purification of a variety of glycoconjugates, including but not limited to a Plasmodium falciparum merozoite glycoconjugate, glycoproteins from the serum of human and animals, including but not limited to $\alpha_2$-macroglobulin from the serum of type B human subjects and bovine thyroglobulin, as well as a variety of other glycoconjugates, including but not limited to laminin, glycoconjugates from basement membranes of mice, rats and rabbits, the surface of 3T3 cells, calf thyroid plasma membranes, the plasma membranes of Ehrlich ascites tumor cells and porcine tissue and organs.

In another embodiment, methods are provided for blocking transplant rejection of porcine tissues and organs transplanted into humans. Porcine tissues and organs comprise the Galα1,3Galβ1,4G1cNAc epitope, the so-called Galili trisaccharide, which prevents their use for transplantation into humans. This epitope is present in most cells of non-primate mammals and new world monkeys but not in humans, apes, or old world monkeys. The methods contemplated in certain embodiments of the present invention include administering a composition comprising a therapeutically effective amount of MOA to a patient receiving porcine tissue and or a porcine organ. The composition may be administered before, during and/or after transplantation to block transplant rejection by the patient. While not to be limited to any particular mechanism, it is believed that MOA binds the Galili trisaccharide, thereby blocking recognition of the trisaccharide by the patient's immune system. In an alternative embodiment, the porcine tissue or organ is contacted with MOA prior to transplantation into the patient. Said contacting is under conditions such that MOA binds the Galili trisaccharide on the porcine tissue or organ. In some embodiments, MOA is contacted with the porcine tissue or organ prior to transplantation into a human patient, and the patient is also administered a composition comprising MOA. Administration of a composition comprising MOA to a patient receiving a transplant comprising a porcine tissue or organ contacted with MOA may occur prior to, during and/or after transplantation. In some embodiments, said administration of a composition comprising MOA results in reduced rejection of the transplant than is (or has been) observed in the absence of MOA treatment. "Reduced rejection" may comprise one or more of the following: longer survival of the transplanted tissue or organ in the human subject, reduced severity of hyperacute rejection, reduced XNA binding the transplanted tissue and reduced activation of platelet and coagulation system mechanisms.

In a further embodiment, therapeutic methods are provided for treating a patient having *Clostridium difficile* Toxin A-induced diarrhea, commonly experienced by patients taking antibiotics, with a composition comprising a therapeutically effective amount of MOA. *C. difficile* Toxin A has been shown to bind to membrane receptors on epithelial cells of the human large intestine and then be internalized by endocytosis. Toxin A has been shown to bind the receptor through the Galα1,3Galβ1,4G1cNAc trisaccharide epitope. Thus, administration of a composition comprising MOA to a subject either experiencing antibiotic-induced diarrhea, or at risk for antibiotic-induced diarrhea (i.e. a subject who is about to begin a course of antibiotic treatment), is expected to be of benefit. While not to be limited to any particular mechanism, it is believed that MOA competes with Toxin A for binding to the Galα1,3Galβ1,4G1cNAc trisaccharide epitope on the receptor, thereby reducing the amount of bound and internalized Toxin A. In some embodiments, administration of a composition comprising MOA (either prophylactically or therapeutically) reduces the duration of antibiotic-induced diarrhea. In some embodiments, administration of a composition comprising MOA (either prophylactically or therapeutically) reduces the severity of antibiotic-induced diarrhea (for example, the patient loses less fluid or has fewer episodes of diarrhea during the course of antibiotic treatment), while in other embodiments, the patient does not experience antibiotic-induced diarrhea.

V. Therapeutic Formulations

As used herein, the terms "therapeutically effective amount" and a "therapeutically effective duration" preferably mean the total amount of each active component of the pharmaceutical composition and a duration of treatment that is sufficient to show a meaningful patient benefit, i.e., treatment, healing, prevention or amelioration of the relevant medical condition, or an increase in rate of treatment, healing, prevention or amelioration of such conditions without undue adverse physiological effects or side effects. The term "therapeutically effective amount," when applied to an individual active ingredient, administered alone, the term refers to that ingredient alone. When applied to a combination, the term refers to combined amounts of the active ingredients, e.g., MOA, or portions of MOA, and other active ingredients, that result in the therapeutic effect, whether administered in combination, serially or simultaneously.

The MOA lectin of the present invention may thus be used in a pharmaceutical composition when combined with a pharmaceutically acceptable carrier. Such a composition may also comprise (in addition to MOA and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s).

In practicing embodiments comprising methods of treatment or use of the present invention, a therapeutically effective amount of MOA of the present invention (or a composition comprising MOA or a portion of MOA) is administered to a patient having a condition to be treated, e.g. porcine tissue transplantation (including but not limited to a porcine cardiac valve replacement). MOA may be administered in accordance with the method of the invention either alone or in combination, including in combination with other conventional therapies. For example, MOA can be used as part of a multidrug regime.

Administration of MOA used in the pharmaceutical composition or to practice the method embodiments of the present invention can be carried out in a variety of conventional ways, such as oral ingestion, inhalation, topical application or cutaneous, subcutaneous, intraperitoneal, parenteral or intravenous injection, transmucosal (including but not limited to intranasal, sublingual, rectal and buccal administration).

When a therapeutically effective amount of MOA is administered orally, the MOA will be in the form of a tablet, capsule, powder, solution or elixir. When administer ed in tablet form, the pharmaceutical composition of the invention may additionally contain a solid carrier such as a gelatin or an adjuvant. The tablet, capsule, and powder contain from about 5 to 95% MOA, and preferably from about 25 to 90% MOA. When administered in liquid form, a liquid carrier such as water, petroleum, oils of animal or plant origin such as peanut oil, mineral oil, soybean oil, or sesame oil, or synthetic oils may be added. The liquid form of the pharmaceutical compositions may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of MOA of the present invention and preferably from about 1 to 50% MOA.

When a therapeutically effective amount of MOA is administered by intravenous, cutaneous or subcutaneous injection, the MOA will be in the form of a pyrogen-free, parenterally acceptable aqueous solution. The preparation of such parenterally acceptable MOA solutions, having due regard to pH, isotonicity, stability, and the like, is within the skill in the art. A preferred pharmaceutical composition for intravenous, cutaneous, or subcutaneous injection should contain, in addition to MOA, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of MOA in the pharmaceutical composition of the present invention will depend upon the nature and severity of the condition being treated, and on the nature of prior treatments which the patient has undergone. Ultimately, the attending physician will decide the amount of MOA with which to treat each individual patient. Initially, the attending physician will administer low doses of MOA and observe the patient's response. Larger doses of MOA may be administered until the optimal therapeutic effect is obtained for the patient, and at that point the dosage is not increased further.

Experimental

The following experiments and examples serve to illustrate certain embodiments and aspects of the present invention and are not to be construed as limiting the scope thereof.

In the disclosure which follows, the following abbreviations apply: M (molar); mM (millimolar); μM (micromolar); nM (nanomolar); mol (moles); mmol (millimoles); μmol (micromoles); nmol (nanomoles); pmol (picomoles); gm (grams); mg (milligrams); μg (micrograms); μg (picograms); L (liters); ml (milliliters); μl (microliters); cm (centimeters); mm (millimeters); μm (micrometers); nm (nanometers); ° C. (degrees Centigrade); bp (base pairs); V (volts); W (watts); RACE (rapid amplification of cDNA ends); hr (hours); min (minutes).

The materials used in the examples below, unless stated otherwise, were obtained from the following sources: G1α1,3Ga1, G1α1,3[L-Fucα1,2]Ga1, and L-Fucα1,2Ga1β1,4G1c were purchased from Dextra Labs (Reading, UK). Ga1β1,6Ga1 was from Sigma (St. Louis, Mo.) and Ga1α1,3Ga1β1,4G1cNAc (linear B-2 saccharide) was from Calbiochem (La Jolla, Calif.). Gala 1,2Ga1 was from Toronto Research Chemicals, Inc. (New York, Ont., Canada). Soluble Ga1α1,3Ga1β-polyacrylamide conjugate was purchased from Glycotech Corporation (Rockville, Md.). Ga1α1,6Ga1 was a gift of Dr. Paul Kovac, Laboratory of Medicinal Chemistry, Section on Carbohydrates, National Institutes Health. Blood group types A (368 PI/WS); B (hnmad BGS 531 PI/WS, pepsin treated); and H (BGS PI/WS) substances were the gift of Dr. Ronald Portez, Rutgers University. Pigeon ovalbumin was a gift from Dr. Y. C. Lee, Department of Biology, Johns Hopkins University. Synsorbs A and B were purchased from Chembiomed Ltd. (Edmonton, Alberta, Canada).

EXAMPLE 1

This example presents the original extraction, isolation and purification procedure used to purify MOA from *M. oreades*. Using this procedure, three MOA polypeptides are recovered: the intact MOA polypeptide of approximately 33 kDa, as well as two) truncated (or "clipped") polypeptides of 23 kDa and 10 kDa.

Fruiting bodies of *M. oreades* mushrooms were harvested in June and August–October 2000, from grassy plots in Ann Arbor, MI, or were purchased from American Mushroom Hunter Corp., Middle Town, N.J. Caps and undamaged stems were cleaned of soil ard debris, and chopped into small pieces. Initially, fresh tissue (45 g) was homogenized at 4° C. in 250 ml PBS containing 10 mM thiourea, 1 g/L ascorbate, 50 mg/L phenylmethylsulfonyl fluoride, and 1–2 g of insoluble polyvinylpolypyrrolidone (Sigma) in a Waring Blender at high speed. The homogenate was stirred for 34 hr in the cold, then strained through 4 layers of cheesecloth, and then centrifuged at 13,000×g for 20 min. The supernatant solution was made 20% saturated with $(NH_4)_2SO_4$ and the resulting solution centrifuged to remove a small amount of precipitate. This supernatant solution was adjusted to 80% saturation with solid $(NH_4)_2SO_4$ and stirred overnight. The precipitate was collected by centrifugation, redissolved in 20 ml of PBS and dialyzed. An affinity column (2.5×15 cm) of melibiose-Sepharose gel, prepared using divinylsulphone coupling, was loaded with the dialyzed fraction and washed with PBS until the absorbance of the effluent at 280 nm became <0.1. Lactose (0.1M) in PBS was then used to displace bound protein. The protein solution so eluted was dialyzed against PBS and passed through a second affinity column, Synsorb-B, consisting of type B trisaccharide $(Gal\alpha1,3[L-Fuc\alpha1,2]Gal\beta O(CH)_8 CONH$-linked to diatomaceous earth. The bound lectin was eluted with 20 mM diaminopropane containing 0.15 M NaCL, pH approximately 11. The "pass through" and displaced protein fractions were combined separately and assayed against a panel of human erythrocytes. Finally, the protein fraction displaced from the Synsorb B column was passed through a column of Synsorb A, which contains covalently-bound type A trisaccharide. A very small amount of material was bound (<5%); it was eluted with 20 mM diaminopropane/0.15 M NaCl. Both fractions were assayed against types A, B and O erythrocytes (see below).

SDS-PAGE analysis was carried out in 12.5% gels (0.8% cross-linked) in tris/glycine buffer, pH 8.8 by the method of Laemmli. Unless otherwise indicated, samples were denatured by boiling in buffer containing 1% SDS and 1% 2-mercaptoethanol. SDS-PAGE analysis of the lectin isolated as described in this example revealed the presence of three bands (FIG. 5): a major band (designated "H") at approximately 33 kDa, a major band (designated "L") at approximately 23 kDa and a significant band (designated "P") at approximately 10 kDa. The absence of 2mercaptoethanol did not alter the pattern of the bands, suggesting the absence of interchain disulphide links. Samples prepared without heating also showed a band at approximately 55 kDa.

Figure 6:
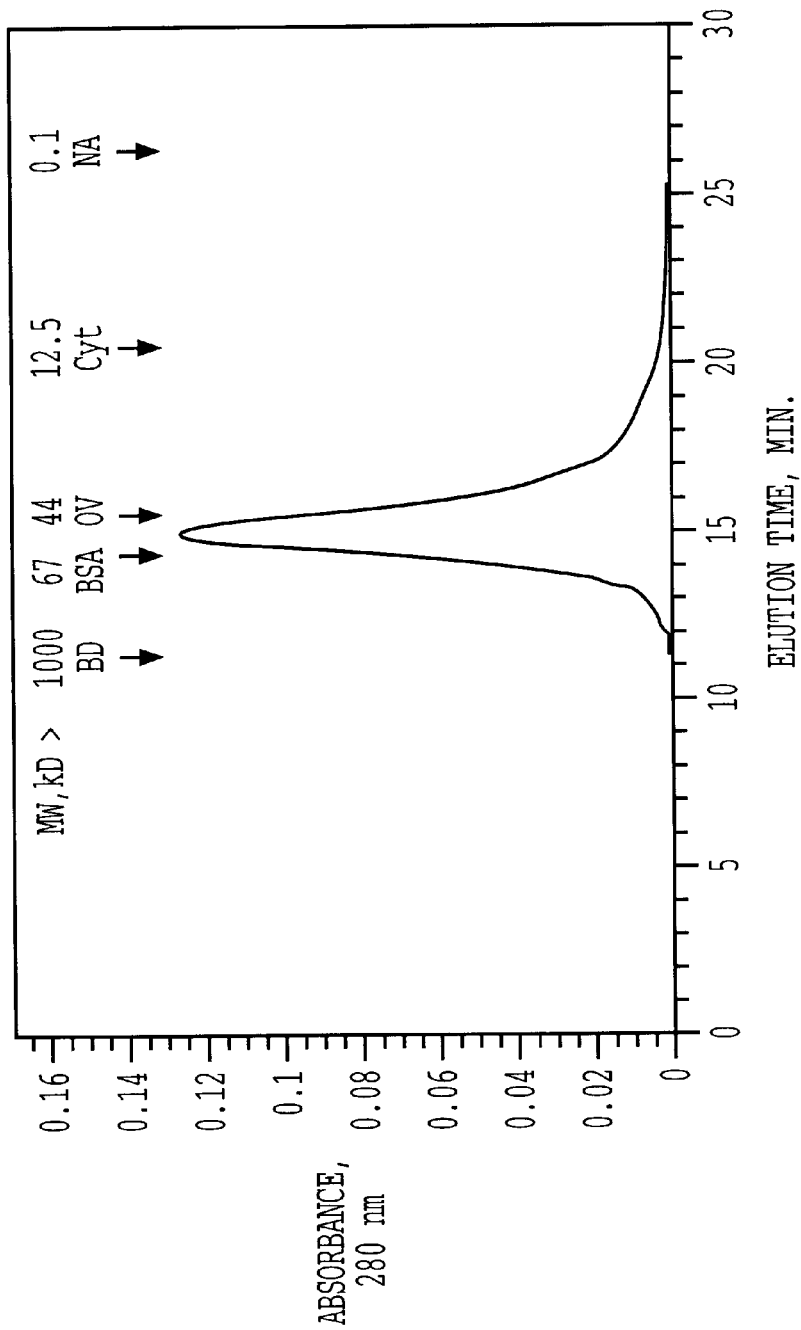
FIG. 6 depicts the elution time of MOA by HPLC. BD, blue dextran), BSA (bovine serum albumin), OV (hen ovalbumin), cyt (cytochrome c), NA (nicotinic acid).

Size exclusion chromatography with HPLC was carried out using a Beckman System Gold equipped with a column (30×0.78 cm) of ProGel-TSK G2000-SWXL (Supelco Bellefonte, Pa.) in PBS with or without added haptenic sugars, at a flow rate of 0.5 ml/min. Samples of 0.1–0.4 mg protein in 0.1 ml were injected, and effluent was monitored at 280 nm. The lectin prepared as described in this example was subjected to size exclusion chromatography by HPLC, and was found to migrate as a single, symmetric peak having the same mobility as *Pisum sativum* and *Xanthosoma sagittifolium* lectins, both known to be of approximately 50 kDa. In the absence of haptenic sugar, the lectin appeared to be of much lower molecular mass based on calibration of the column with cytochrome c, ovalbumin and bovine serum albumin. In the presence of 0.1 M lactose, but not methyl α-mannoside, MOA migrated slightly faster the n ovalbumin (FIG. 6), at an apparent mass of 49.5 kDa, suggesting that the lectin interacted weakly with the column matrix, despite its being a silica-based non-carbohydrate matrix.

The lectin prepared as described in this example was subjected to MALDI-TOF mass spectrometric analysis, wherein mass ions corresponding to the three bands were detected. Within the limits of the mass calibration, the sum of the two smaller molecular masses (corresponding to the L and P polypeptides) approximates the larger molecular mass of the H polypeptide. Mass spectrometric analysis of tryptic peptides from the various bands (i.e. H, L and P), and total amino acid analysis also support the conclusion that the two lighter bands, L and P, are fragments of the intact band H. No significant amounts of any amino acids were obtained during several cycles of automated amino acid sequencing of the H and L bands, indicating that they possess blocked N-termini. The P band released small amounts of several amino acid derivatives at some of the cycles, but no single sequence was detected, suggesting that it is also largely blocked and may be heterogenous.

EXAMPLE 2

This example presents a modification to the MOA extraction, isolation and purification protocol presented in example 1. This procedure, which is the presently preferred method for extracting, isolating and purifying MOA from *M. oreades*, uses a protease inhibitor cocktail, to prevent protease activity, and also takes steps to prevent possible oxidation of aromatic side chains.

The extraction procedure as describe in example 1 is modified by including a protease inhibitor cocktail (product P8215, Sigma) at the level of 1 ml/L extract buffer in place of the phenylmethylsulfonyl fluoride, eliminating $Ca^{2+}$ from all buffers, and including 1.25 mM EDTA in all buffers, as well as carrying out the extraction and ammonium sulfate precipitations under an atmosphere of argon.

This modified procedure led to the isolation of a homodimer of two identical subunits, lacking any detectable 23 kDa and 10 kDa polypeptides, and having no absorbance above 3201 nm.

EXAMPLE 3

This example presents an analysis of hemagglutination activity and inhibition of hemagglutination using MOA prepared according to the method presented in Example 1. It should be noted that substantially the same, if not identical, hemagglutination results are expected using MOA prepared according to the procedure presented in Example 2, or using recombinantly expressed and purified MOA.

Hemagglutination assays were carried out using formaldehyde-treated erythrocytes in V-well microtitre plates as described by Mo et al. [*J. Biol. Chem* 275:10623 (2000)], herein incorporated by reference. Titres were recorded as the greatest dilution of the lectin solution yielding visible agglutination. Agglutination of Ehrlich ascites tumor cells (grown in in vitro culture) was observed microscopically.

The hemagglutinating activity against types A, B, and O cells, and several other cell types, is presented in Table 2. Hemagglutination activity was unchanged by extensive dialysis of the lectin and assay in metal-free buffer containing EDTA, indicating the absence of a divatent metal ion requirement. As noted in Example 2, subsequent assays and purifications routinely used metal-free buffers containing EDTA.

EXAMPLE 4

This example presents quantitative precipitation assays and hapten inhibition assays of MOA (prepared according to the method presented in Example 1) with soluble cyst group substances and other glycoconjugates. It should be noted that although the experiments presented in this example used the MOA lectin prepared according to the method of Example 1, substantially the same, if not identical, results are expected using MOA prepared according to the method of Example 2, or using recombinantly expressed MOA.

For quantitative precipitation assays, 20 µg of MOA and increasing amounts of glycoprotein or polysaccharide were used in a total volume of 120 to 200 µL, all in PBS/0.15 M NaCl. Quantitative carbohydrate hapten inhibition assays were conducted by adding increasing amounts of haptens to a mixture of MOA (20 µg) and type B blood group substance (5.0 µg). The reactions were incubated at 37° C. for an hour and then at 4° C. for 48 hours followed by centrifugation of the precipitates, washing, and determination of protein by the Lowry method [Lowry, O. H. et al., *J. Biol. Chem.* 193, 265–275 (1951)].

Figure 7:
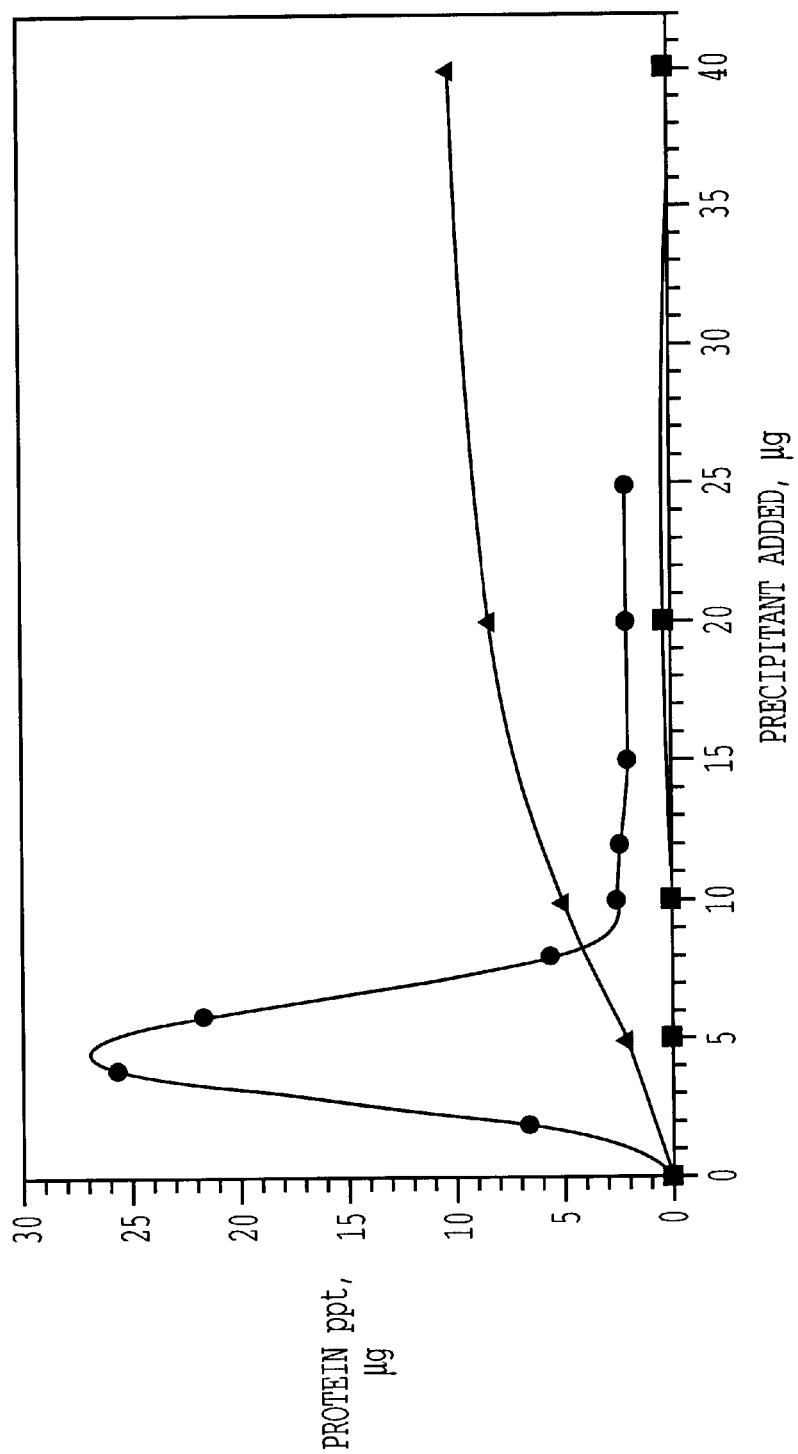
FIG. 7 depicts the results of quantitative precipitation assays of MOA with blood group substances.

The results of quantitative precipitation assays of MOA with soluble cyst blood group substances are shown in FIG. 7. Varying amounts of blood group substances from 0 to 200 µg were incubated with 20 µg of MOA in a total volume of 150 µl of PBS (pH 7.2). After 48 hr at 4° C., the amounts of protein precipitated were quantified as described above. Solid squares indicate group A substance, solid circles indicate group B substance, and solid triangles indicate group O substance. As can be seen in FIG. 7, MOA reacts strongly with human blood type B substance, not at all with type A substance, and rather weakly with type H substance.

Figure 8:
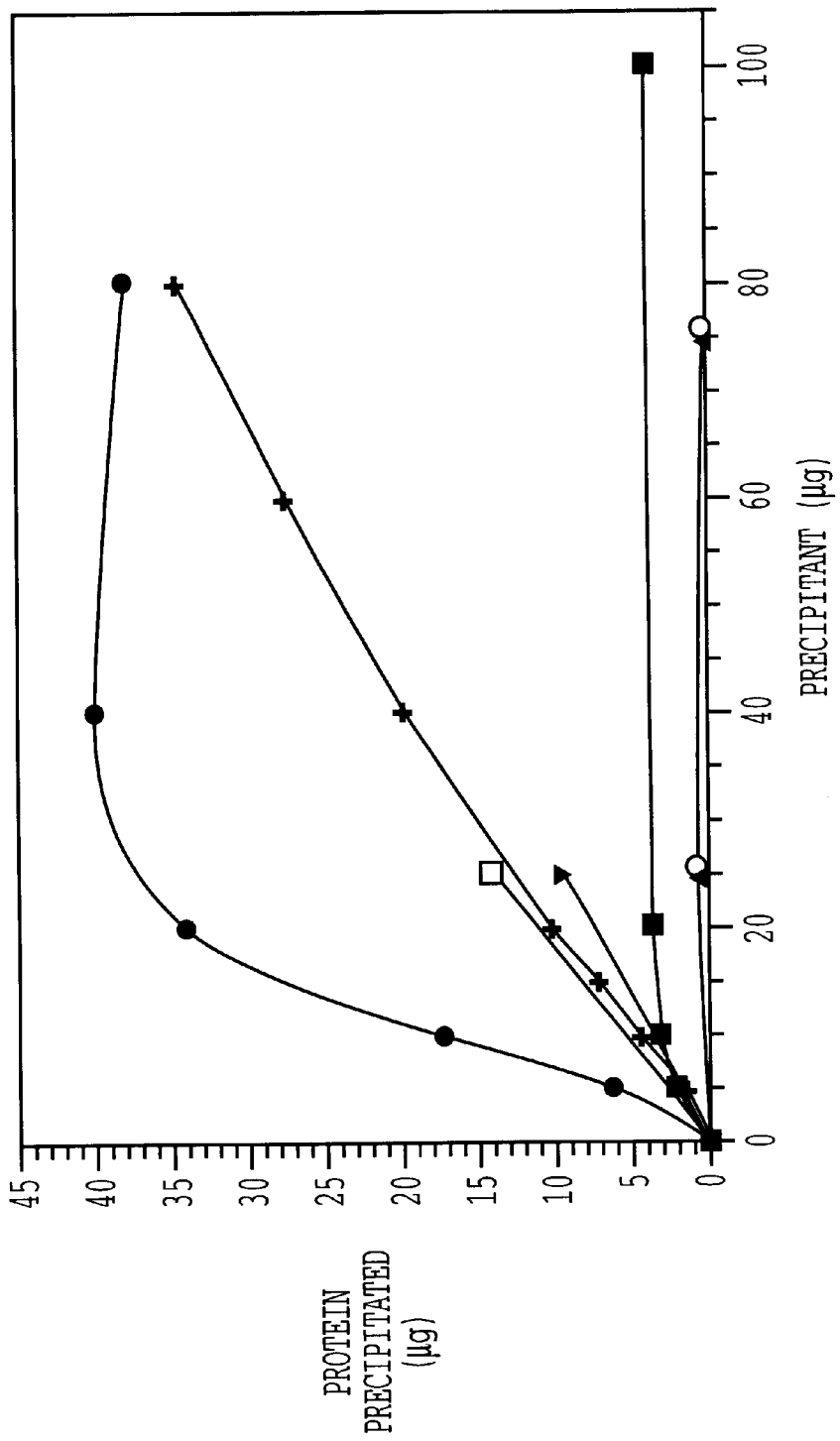
FIG. 8 depicts the results of quantitative precipitation assays of MOA with glycoconjugates.

The results of quantitative precipitation assays of MOA with glycoconjugates are shown in FIG. 8. FIG. 8 also shows, for comparison purposes, the interaction of the *Giffonia simplicifolia* I-B$_4$ isolectin (GS I-B$_4$) with selected glycoconjugates. Various amounts of glycoconjugates, ranging from 0 to 100 µg were incubated with 20 µg of lectin in a total volume of 150 µl of PBS (pH 7.2). After 48 hr at 4° C., the amounts of protein precipitated were quantified, as described above. Solid circles indicate MOA interaction with laminin, solid crosses indicate MOA interaction with bovine thyroglobulin, solid squares indicate MOA interaction with *C. alata* galactomannan, solid triangles indicate MOA interaction with pigeon ovalbumin, open circles indicate MOA interaction with GalNAcα1,3Galβ-polyacrylamide, open squares indicate GS I-B$_4$ interaction with pigeon ovalbumin and closed inverted triangles indicate GS I-B$_4$ interaction with GalNAcα1,3Galβ-polyacrylamide.

As shown in FIG. 8, MOA reacted strongly with laminin, as well as with bovine thyroglobulin (both of which have G1α1,3Galβ1,4G1cNAc-end groups). MOA did not give precipitation with pigeon ovalbumnin (which contains G1α1,4Gal end groups), thereby demonstrating the specificity of MOA for Galα1,3Gal groups. MOA also did lot recognize the blood group type A disaccharide (GalNAcα1,3Gal) as shown by, the lack of precipitation with this disaccharide-polyacrylamide glycoconjugate. MOA did not precipitate the galactomannan from *Cassia alata* (which contains multiple α-galactosyl end groups), illustrating its lack of reactivity with single sugar residues. In contrast, the GS I-B$_4$ isolectin reacted strongly with pigeon ovalbumin and the blood group type A disaccharide-polyacrylamide conjugate.

Figure 9:
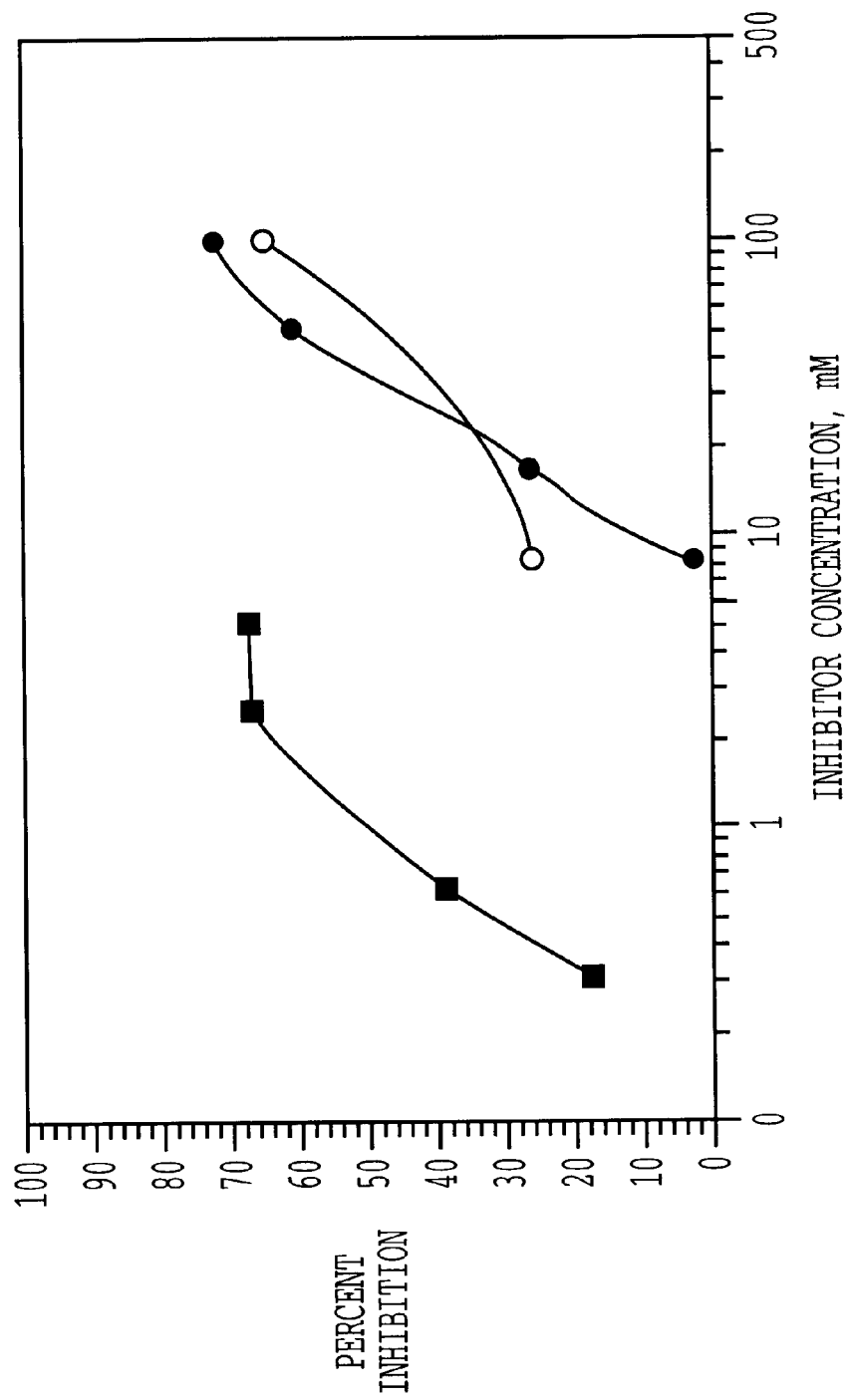
FIG. 9 depicts sugar hapten inhibition of MOA-blood group substance precipitation.

Results of sugar hapten inhibition of MOA-blood group B substance precipitation are shown in FIG. 9. The concentrations of the inhibitory sugars indicated in the figure were incubated with 20 µg of MOA in a total volume of 145 µl of PBS for 20 min, followed by addition of 5 µg of B substance. After 48 hr at 4° C., the amounts of protein precipitated were quantified. Solid circles indicates N-acetyllactosamine, open circles indicate melibiose and solid squares indicate Galα1, 3Gal (B disaccharide).

EXAMPLE 5

This example presents isothermal titration calorimetry data for sugar ligand binding to MOA, prepared according to the method presented in Example 1. It should be noted that all three types of MOA preparations have been used in similar experiments, and that while the MOA prepared according to the method of Example 2 and the recombinant preparations give somewhat higher binding constants, the relative values for various ligands are the same.

Isothermal titration calorimetry was carried out as described by Mo et al. *Eur. J. Biochem.* 268: 2609 (2001), except that 1.0 ml of lectin solutions containing 0.08–0.12 mM H, L and P polypeptides were used. As this volume underfills the titration cell, variable volume calculations were applied, using the Bindworks software installed in the instrument. As can be seen, isothermal titration calorimetry gave approximately the same results as the hemagglutination assays and quantitative precipitation assays presented in the previous examples, however, the data obtained by calorimetry is more precise. Table 3 shows that the blood group B disaccharide, G1α1,3Gal was an excellent ligand with a Ka $6.0 \times 10^3$ M$^{-1}$, whereas the isomeric disaccharides Gal+1, 2Gal, Gal+1,4Gal and G1α1,6Gal bound poorly or not at all. Addition of a G1cNAc group to the reducing end of Galα1,3Gal to give Gal+1,3Galβ1,4G1cNAc increased the binding by approximately 50% to Ka $9.7 \times 10^3$ M$^{-1}$. Similarly, adding an L-fucosyl group to the disaccharide to afford the blood group B branched trisaccharide (G1α1,3 [L-Fucα1,2]Gal) enhanced its affinity to MOA 4-fold (Ka $3.6 \times 10^4$ M$^{-1}$). Finally, the trisaccharide L-Fucα1,2Galβ1, 4G1c (fucosyllactose), related to the blood group H trisaccbaride, was assayed. It appears that the L-fucosyl residue makes a significant contribution to the binding affinity of the essentially inactive lactose (Ka=185 M$-1$) (see Table 3). While not to be limited to any particular mechanism, it is believed that this may be the reason that MOA recognizes and agglutinates human O erythrocytes to a limited extent, and gives a weak precipitin curve with blood group H substance.

EXAMPLE 6

This example demonstrates the use of immobilized MOA as an affinity reagent as exemplified by the fractionation of glycoconjugates from human sera. In this example, MOA was prepared according to the method presented in Example 2. It should be noted that recombinantly expressed MOA and MOA prepared according to the method of Example 1 can also be used in the same manner, with the same results expected.

The materials for this example were obtained as follows. Cyanogen bromide-activated Sepharose 4B, bovine serum albumin, asialofetuin, bovine thyroglobulin, coffee bean α-galactosidase and rabbit antibody against α$_2$-macroglobulin were obtained from Sigma (St. Louis, Mo.). Antiserum against ricin agglutinin was purchased from Vector Labs, Inc. (Burlingame, Calif.). Galactomannan and laminin were available from previous studies. *Eunomys europaeus* lectin was purified on Synsorb H from Chembiomed (Ontario, Canada). Pigeon ovalbumin was the gift of Dr. Y. C. Lee, Department of Biology, Johns Hopkins University. Serum samples were prepared from the blood of pig, rat, rabbit, and six human volunteers (see Table 4). For serum recovery, blood drawn into a plain vacutainer tube was placed at 37° C. for 20 min. The resultant clot was dislodged using an applicator stick and removed by centrifugation at 1000×g to afford clear sera.

MOA was immobilized on cyanogen bromide-activated Sepharose 4B as follows. 1.5 g of cyanogen bromide-activated Sepharose 4B was allowed to swell in 100 ml of 1 mM HCl solution for 30 min. The supernatant was removed and the swollen beads (6 ml) were filtered on a sintered funnel, washed several times with 100 ml of 1 mM HCl and finally with 20 ml of 0.1 M sodium bicarbonate buffer, pH 8.3, containing 0.5 M sodium chloride. The beads were quickly transferred to a plastic bottle containing 16.2 mg MOA in the same buffer (10 ml) containing 0.2 M lactose. The plastic bottle was shaken at room temperature for 6 hr and at 4° C. overnight. The beads were filtered on a sintered glass funnel, washed with the coupling buffer, and then shaken in 1 M ethanolamine (12 ml) at room temperature for 2.5 hr to cap all of the unreacted iminocarbonate groups. The beads were filtered, washed alternately with the coupling buffer then sodium acetate buffer (0.1 M, pH 4.0 containing 0.5 M NaCl) four times. A column (1×7 cm) packed with the beads was finally washed with PBS containing 0.04% sodium azide. The beads contained 2.3 mg MOA per ml Sepharose 4B, based on MOA remaining in solution.

In order to assess the binding of various glycans, glycoconjugates and serum samples to MOA-Sepharose, the following general procedure was used. The MOA-Sepharose column was loaded with glycan, glycoconjugate or serum sample (0.6–5 ml) and washed with PBS (15 ml). The bound components were eluted with 20 mM 1,3-diaminopropane in 0.15 M NaCl (15 ml). The fractions collected (1 ml) were neutralized with 1 M phosphoric acid (approximately 16 μl), and analyzed by either absorbance at 280 nm for protein, or by phenol-sulfuric acid assay, as described by Dubois et al. [Anal. Chem. 28: 350 (1956)] for the glycan. The column was finally washed thoroughly with PBS. The fractions containing the bound components were pooled and concentrated by Amicon ultrafiltration (Millipore Corp., Bedford, Mass.) using a membrane (YM10) of 10,000 molecular weight cut-off.

Figure 10A:
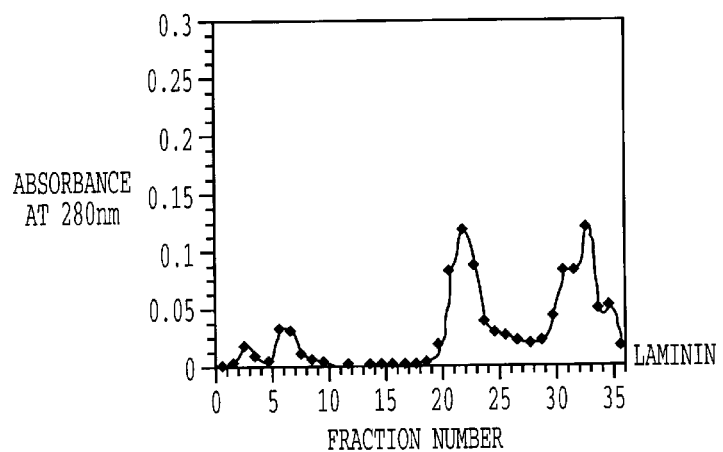
FIG. 10A depicts the elution profile of laminin from MOA-Sepharose 4B.
Figure 10B:
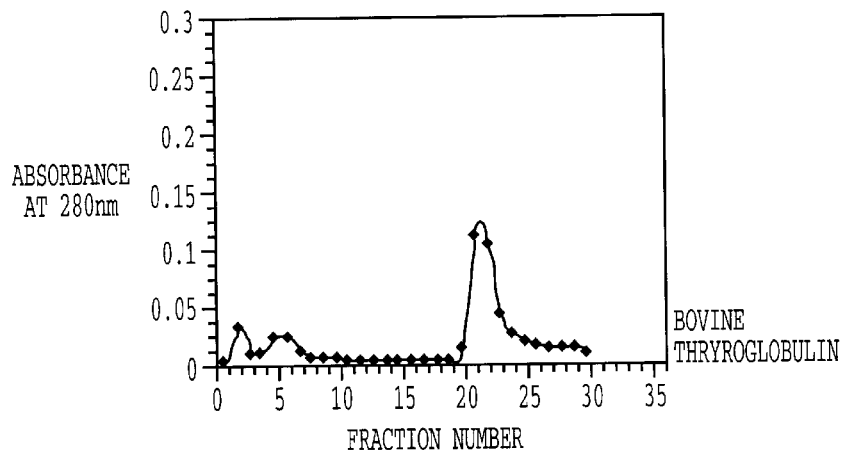
FIG. 10B depicts the elution profile of bovine thyroglobulin from MOA-Sepharose 4B.

Various glycans and glycoconjugates were initially applied to the MOA-Sepharose column to confirm the carbohydrate binding specificity of the immobilized MOA. Laminin purified from the EHS sarcoma (FIG. 10A) and bovine thyroglobulin (FIG. 10B) (both of which have multiple Galα1,3Galβ1,4GlcNAc end groups) bound tightly to immobilized MOA and were eluted with 20 mM diaminopropane. The appearance of two peaks in the elution profile of laminin reveals heterogeneity in its glycan structure (FIG. 10A).

Figure 10C:
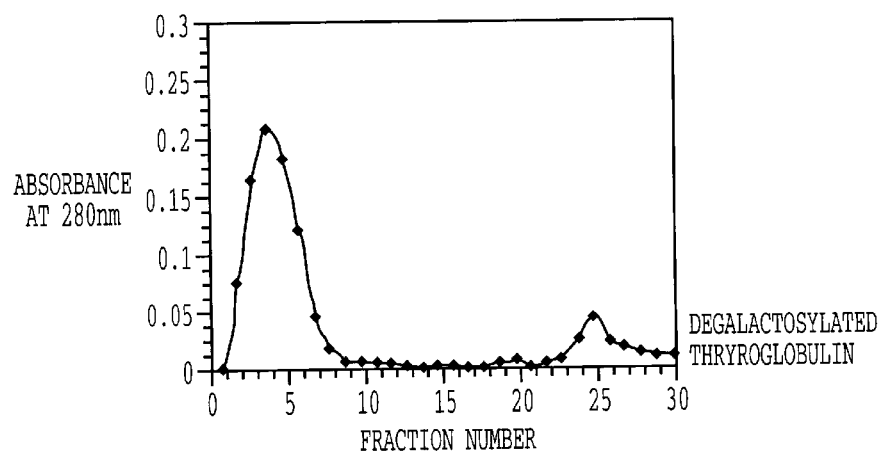
FIG. 10C depicts the elution profile of degalactosylated thyroglobulin from MOA-Sepharose 4B.
Figure 10D:
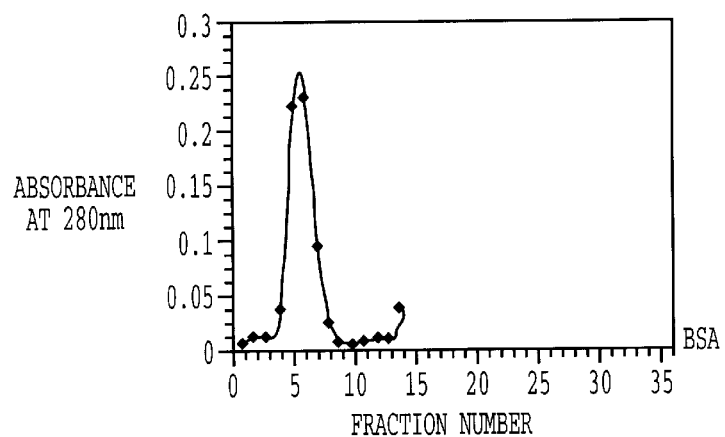
FIG. 10D depicts the elution profile of BSA from MOA-Sepharose 4B.
Figure 10E:
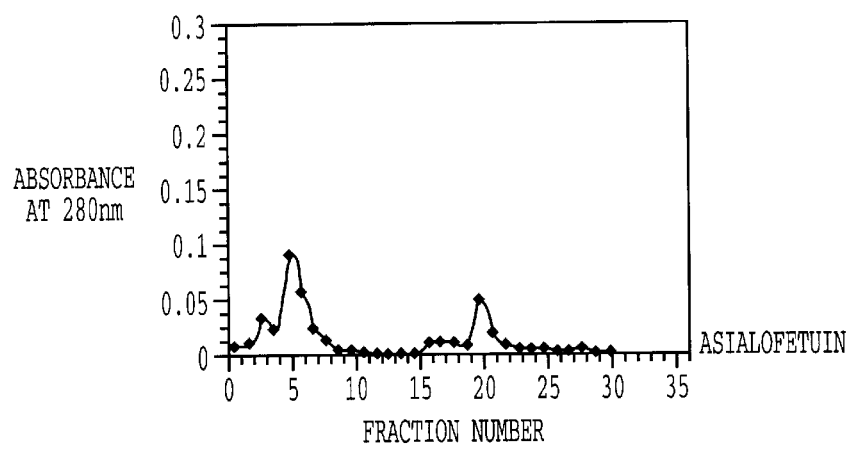
FIG. 10E depicts the elution profile of asialofetuin from MOA-Sepharose 4B.
Figure 10F:
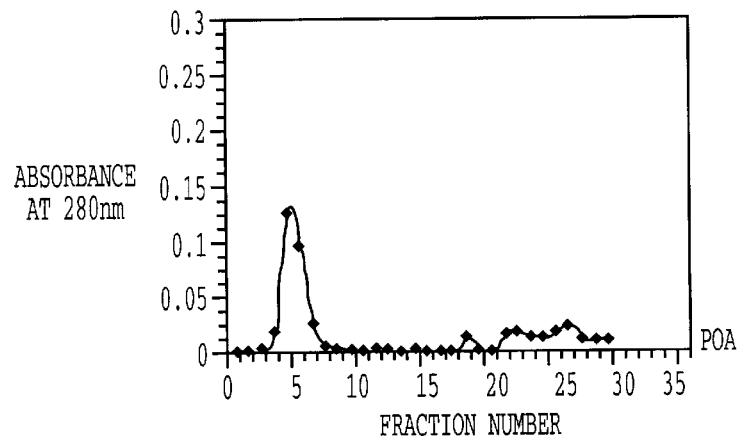
FIG. 10F depicts the elution profile of pigeon ovalbumin from MOA-Sepharose 4B.

To prepare α-galactosidase-digested bovine thyroglobulin, 2 mg of bovine thyroglobulin was incubated at 37° C. in 200 μl of 0.1M sodium phosphate buffer (pH 6.5) to which was added green coffee bean α-galactosidase solution (18 μl, 1 IU). The reaction was allowed to proceed for 8 hr, followed by storage at 4° C. The degalactosylated bovine thyroglobulin passed through the column (FIG. 10C), as did asialofetuin (FIG. 10E), both of which contain terminal Galβ1,4GlcNAc saccharide residues. Pigeon ovalbumin, a glycoprotein which contains Glcα1,4Gal1-terminated N-glycans similarly did not bind to the MOA-Sepharose column (FIG. 10F). Blood group H substance, which has terminal Fucα1,2Galβ1,4GlcNAc chains also failed to bind MOA-Sepharose (results not shown), although the trisaccharide Fucα1,2Galβ1,4Glc exhibited low but measurable binding in solution (as noted in the examples above). Considered together, these results indicate the trisaccharide specificity of MOA and the requirement of the Galα1,3Gal linkage for binding. Galactomannan, which also has Glcα1,6Man branches, also failed to bind MOA-Sepharose (results not shown).

Figure 11A:
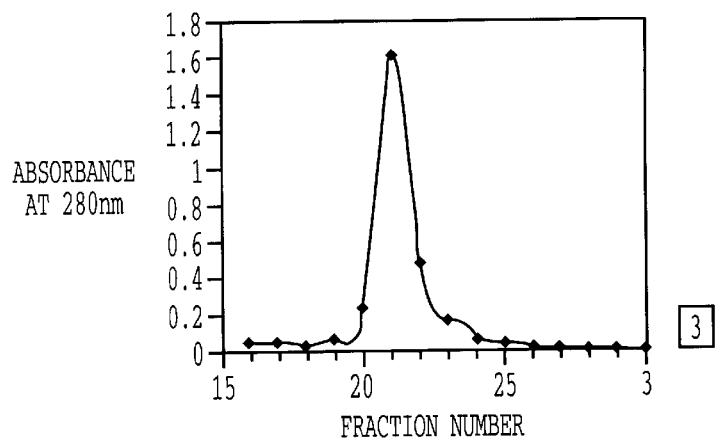
FIG. 11A depicts the elution profile of serum components from volunteer 3.
Figure 11B:
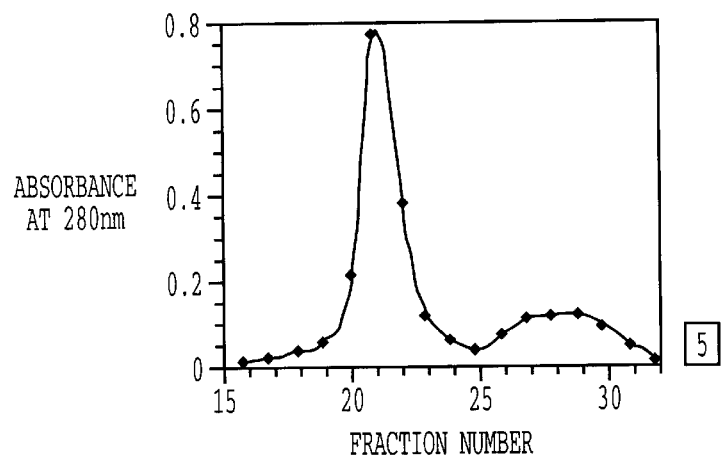
FIG. 11B depicts the elution profile of serum components from volunteer 5.
Figure 11C:
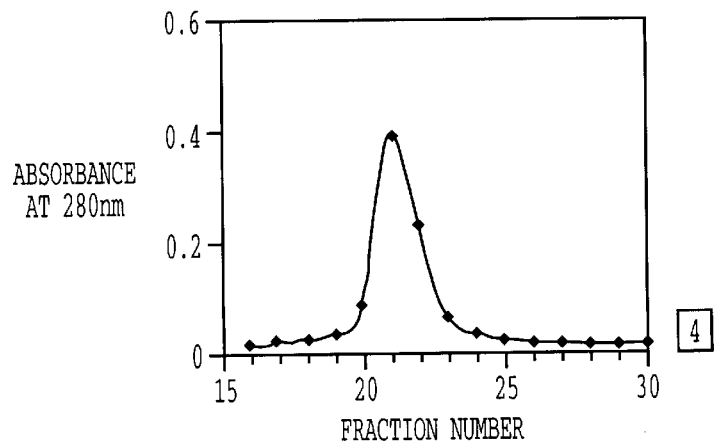
FIG. 11C depicts the elution profile of serum components from volunteer 4.
Figure 11D:
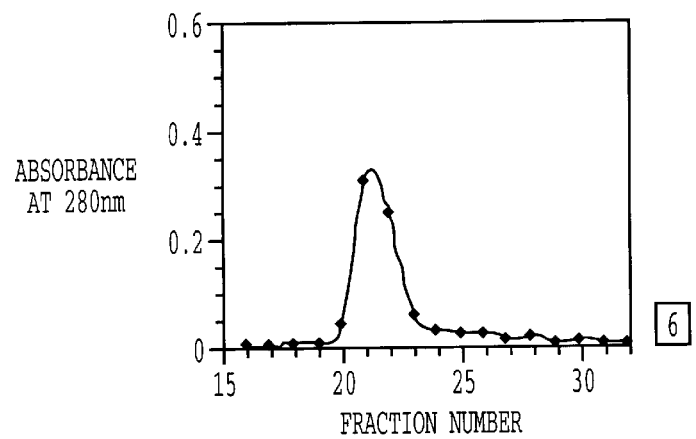
FIG. 11D depicts the elution profile of serum components from volunteer 6.
Figure 11E:
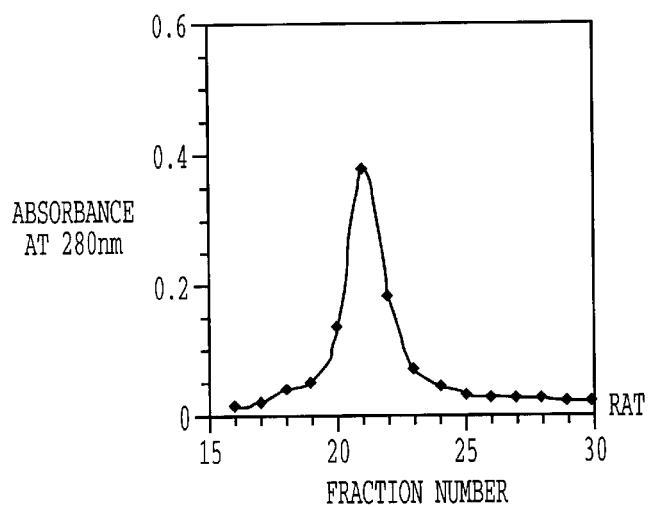
FIG. 11E depicts the elution profile of se rum components from rat.
Figure 11F:
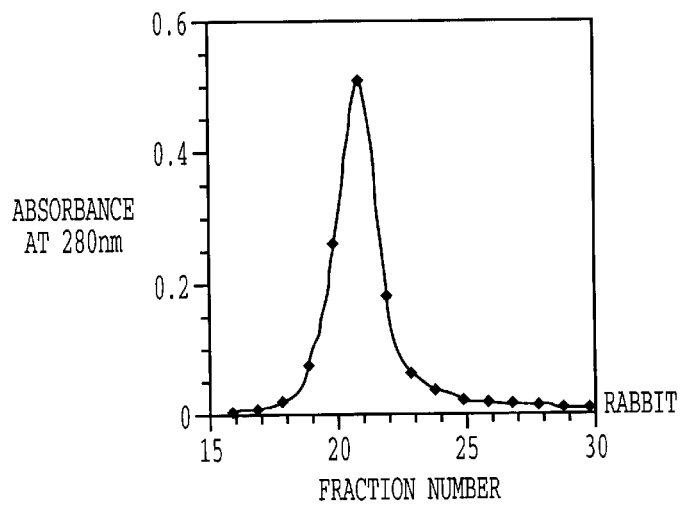
FIG. 11F depicts the elution profile of serum components from rabbit.
Figure 11G:
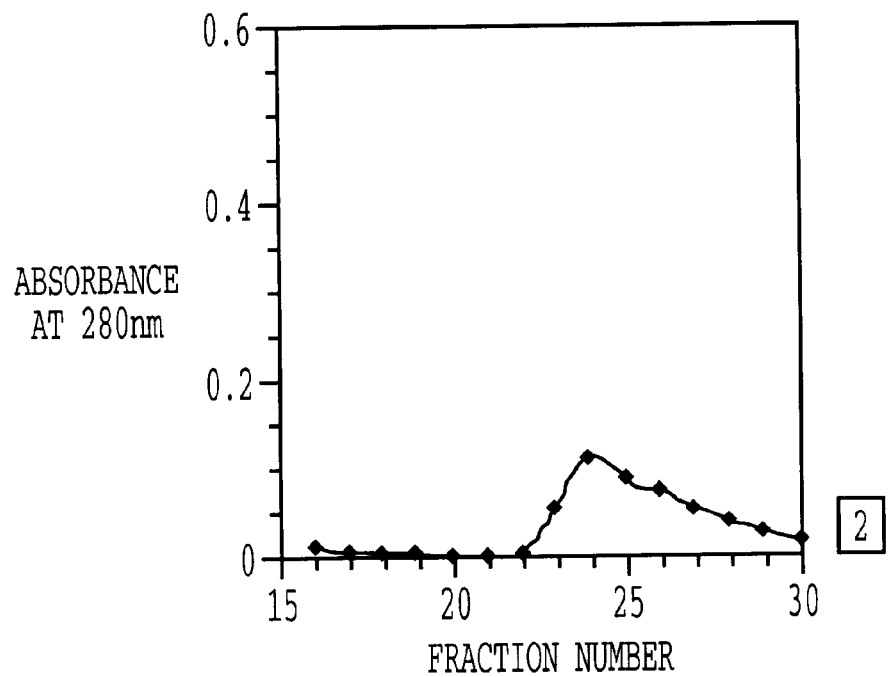
FIG. 11G depicts the elution profile of serum components from volunteer 2.
Figure 11H:
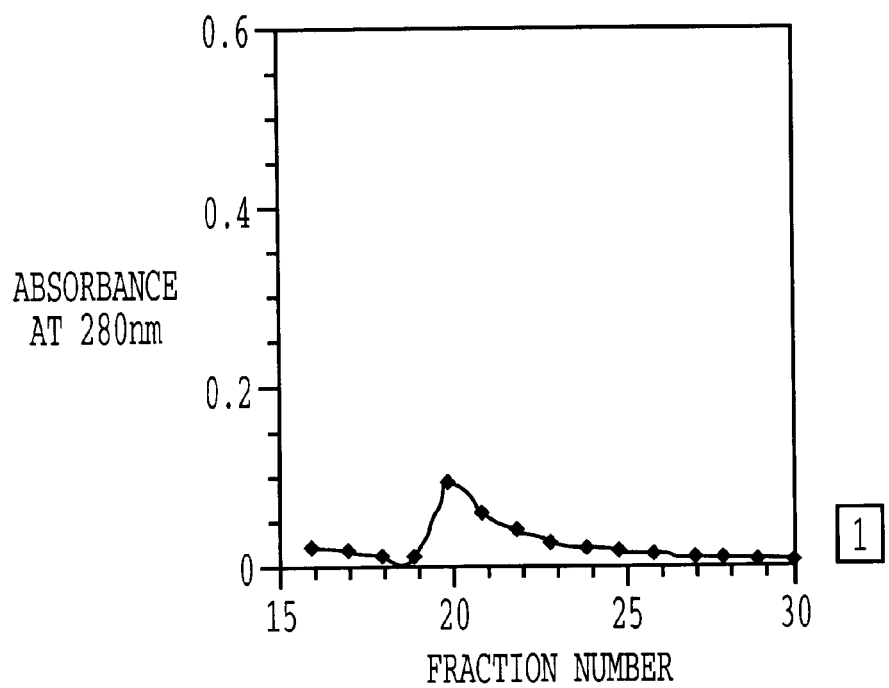
FIG. 11H depicts the elution profile of serum components from volunteer 1.

Interactions of various blood sera with immobilized MOA were also examined. Serum samples obtained from human individuals belonging to blood groups A, B and O as well from animals (pig, rat and rabbit) were chosen for study. All human volunteers were of the secretor type. After applying the serum sample to the column, elution was conducted first with PBS (15 fractions of varying volume) to wash off the unbound components. Subsequent elution with 20 mM diaminopropane in 0.15 M NaCl afforded the bound components, collected in 15 fractions of 1 ml volume. As expected, the amount of bound protein was minimal for the blood group A sera of volunteer 2 (FIG. 11G) and volunteer 1 (FIG. 11H), whereas a significant amount was bound in the case of the three blood group B individuals [volunteer 3, FIG. 11A; volunteer 4, FIG. 11C; volunteer 5, FIG. 11B] as well as the of the O type [volunteer 6, FIG. 11D). Interestingly, the elution profile of the bound material of the serum of volunteer 5 shows the presence of a major band and a minor fractions, with the latter having high affinity (FIG. 11B).

SDS-PAGE analysis (carried out in 7.5% gels [0.8% crosslinked] using tris/glycine buffer, pH 8.8, by the procedure of Laemmli with denaturation of samples by 5 min of boiling in buffer containing 1% SDS and 1% 2-mercaptoethanol) of the bound fractions of the various sera revealed both qualitative and quantitative differences in the protein components. Most importantly, the major band seen in the case of volunteers 3, 4 and 5 corresponds to a protein with a molecular weight of approximately 185 kDa This component showed no detectable reaction with anti-B antibody. Protein sequencing of this component led to its identification as $\alpha_2$-macroglobulin. Its identity was confirmed by the formation of a sharp precipitin band upon immunodiffusion against rabbit anti-$\alpha_2$-macroglobulin. Treatment of the fractions containing principally $\alpha_2$-macroglobulin abolished its binding to the immobilized MOA column.

To further probe the nature of the $a_2$-macroglobulin moiety reactive with MOA, two additional lectins were used: *Euonymus europaeus* and *Ulex europaeus* I lectins. The *Euonymous* lectin has complex specificity, and recognizes, among others, terminal Gal linked a 1,3 to a subterminal sugar. This lectin gave precipitin bands upon agar gel diffusion against the $\alpha_2$-macroglobulin from volunteers 4 and 5. α-Galactosidase-digested glyocprotein from volunteer 4 precipitated in gel with Ulex I, but not with Lotus lectin), strongly suggesting the presence of L-Fucα1,2Gal groups.

The isolation and partial characterization of $\alpha_2$-macroglobulin containing blood group B epitopes from the serum of type B individuals confirms an earlier report of the presence of covalently-linked ABO (H) blood group antigens on human plasma $\alpha_2$-macroglobulin and von Willebrand factor [Matsui et al. *Blood* 82: 663 (1993)].

It is expected that immobilized MOA will prove to be a very valuable probe for the detection, separation and characterization of biomedically relevant glycoconjugates.

EXAMPLE 7

This example provides a method to label MOA with fluorescein, and use the fluorescein-labeled MOA in binding and detection assays.

MOA prepared by the method presented in Example 1 was fluorescently labeled using fluorescein isothiocyanate (Sigrna, St. Louis, MO.) at pH 9.5 in the presence of 0.2 M lactose, followed by exhaustive dialysis.

Figure 12:
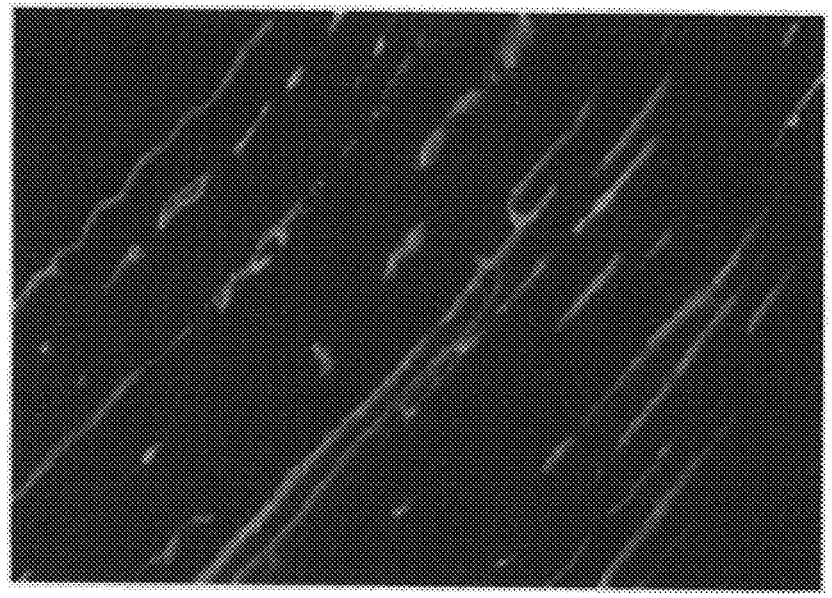
FIG. 12 shows a section of porcine striated skeletal muscle stained with fluorescein-labeled MOA. Image size is 370×260 μm.

To stain a section of porcine skeletal muscle, a solution of fluorescein-labeled MOA (8 µg/ml) in PBS containing 2% goat serum and 0.2% triton X-100, in the absence or presence of 20 mM linear B6 trisaccharide, was applied to a cryostat section (10 microns, fixed in paraformaldehyde) of porcine skeletal muscle. After incubating at room temperature for 2 hr, the staining solution was removed, the section was washed with PBS and examined under a fluorescent microscope. As can be seen in FIG. 12, fluorescein-labeled MOA stained porcine striated skeletal muscle, with endothelial cells lining the capillaries being the significant structures stained by the lectin. Incubation of the staining solution in the presence of 20 mM linear B6 trisaccharide essentially abolished staining, indicating specific binding of the fluorescein-labeled MOA to the porcine tissue.

A similar procedure was used to stain a human type A blood smear infected with *Plasmodium merozoites*. The blood smear was prepared with acetone. The procedure for staining was similar to that used for the porcine muscle staining described above, except that no detergent was included in the staining solution. The *Plasmodium falciparum* merozoites in the blood smear were stained by the fluorescein-labeled lectin.

EXAMPLE 8

This example presents the cloning and recombinant expression of the MOA cDNA sequence. The materials and methods used for this example are as follows.

Peptide sequencing and analysis—Peptide sequence was determined by the Macromolecular Structure facility at Michigan State University. Briefly, purified protein was digested with trypsin or endoproteinase Asp-N. Proteolytic fragments were bound to a C-18 column and eluted with a gradient of acetonitrile. Purified peptides were then sequenced by Edman degradation.

RNA isolation and Northern Analysis—*Marasmius oreades* (fairy-ring) mushrooms were collected in grassy plots in Ann Arbor, Mich., frozen immediately in dry ice, and stored at –80° C. until extraction. The frozen tissue was ground under liquid nitrogen to a medium-fine powder with a mortar and pestle resting in dry ice. Subsequent steps in the RNA purification followed recommendations given with the Plant RNA Isolation Aid as an accessory to the RNAqueous-Midi kit (Ambion). Using this protocol, 7.2 µg of total RNA could be isolated per gram of mushroom.

Oligonucleotides for RT-PCR were designed from the available peptide sequences. The two regions with lowest degeneracy are within a region of four peptides whose sequences overlap one another. The forward primer (5'-GGNTGGCARTTYACNCC-3' [SEQ ID NO: 24]) was reverse translated from the amino acid sequence GWQFTP [SEQ ID NO: 25]. The reverse primer (5'-ARYTGRTGCCARTTDAT-3' [SEQ ID NO: 26]) is the reverse complement of the reverse translated amino acid sequence INWHQL [SEQ ID NO: 27]. The degeneracies of the forward and reverse primers are 64 and 48-fold, respectively. RT-PCR was conducted with M-MLV reverse transcriptase (GibcoBRL) and Amplitaq Gold polymerase (Applied Biosystems). Template mRNA was purified from 0.86 µg total RNA using the mRNA capture kit (Roche). A PCR product of appropriate size (~0 bp) was cloned using the TA TOPO PCR cloning kit (Invitrogen). Sequencing of this product yielded a total of II unambiguous bases.

5' and 3' RACE was performed essentially as described in the FirstChoice RLM-RACE kit (Ambion). Two overlapping primers were designed for each 5' and 3' RACE. These primers include all or part of the 11 unambiguous bases. The two primers used for subsequent amplification steps in 5' RACE (1: 5'-ARYTGRTGCCARTTRATCGT-3' [SEQ ID NO: 28]; 2: 5'-TGCCARTTRATCGTGTCTGG-3' [SEQ ID NO: 29]) are 32- and 4-fold degenerate respectively, with the degeneracy weighted towards the 5' ends. Similarly, the two primers used for 3' RACE (1:5'-GGNTGGCARTTYACRCCAGA-3' [SEQ ID NO: 30] and 2:5'-CARTTYACRCCAGACACGAT-3' [SEQ ID NO: 31]) are 3.2 and 8-fold degenerate, respectively.

For Northern analysis, total RNA (10 µg) was run on a pre-run formamide gel and transferred to a nylon membrane (Nytran) with the Bios Blotting System. The cDNA probe was generated by random primer labeling with Kienow (Roche) incorporating $^{32}$PDATP (Perkin Elmer). The template used was a full-length coding sequence PCR product. The blot was probed and washed according the membrane manufacturer's protocol and exposed to film for 2 hours.

Expression and characterization of recombinant MOA: A full-length PCR product incorporating NdeI and EcoRI into its forward and reverse primers, respectively, was cloned into PCR Blunt II using topoisomerase (Invitrogen) and subsequently shuttled into an IPTG inducible pT7 expression vector (MOApT7LO). Recombinant MOA was expressed in a Nova Blue DE3 strain of *E. coli*. Expressing bacteria were collected by centrifugation and resuspended in a lysis buffer consisting of 50 mM $NaH_2PO_4$, 300 mM NaCl, 10 mM imidizole, 10mM 2-mercaptoethanol, 1 mM phenylmethylsulfonyl fluoride, 1% NP-40, and a protease inhibitor cocktail. The extract was twice run through a french press. The insoluble fraction was removed by centrifugation (10,000×g, 15 min).

Purification of recombinant MOA and native intact MOA-Recombinant MOA was purified from the soluble fraction by absorption on a column of melibiose-Sepharose and elution by lactose. Further purification was carried out on an affinity column of Synsorb B. Except for the diaminopropane elution, all affinity purifications were carried out in PBS, pH 7.2, containing 1.25 mM EDTA. After purification, lectin solutions were dialyzed against distilled water and lyophilized. Salt-free lyophilisates were readily soluble in distilled water or buffer, with retention of full agglutinating activity. Intact native MOA was prepared with a purification procedure (Example 2) that utilized a protease inhibitor cocktail (product P8215, Sigma, St. Louis, Mo.) which was added at the level of 0.1 ml/100 ml extract buffer (instead of phenylmethylsulfonyl fluoride), all buffers lacked $Ca^{++}$ and contained 1.25 mM EDTA, and the initial extraction and ammonium sulfate fractionations were carried out under an atmosphere of argon.

Figure 13:
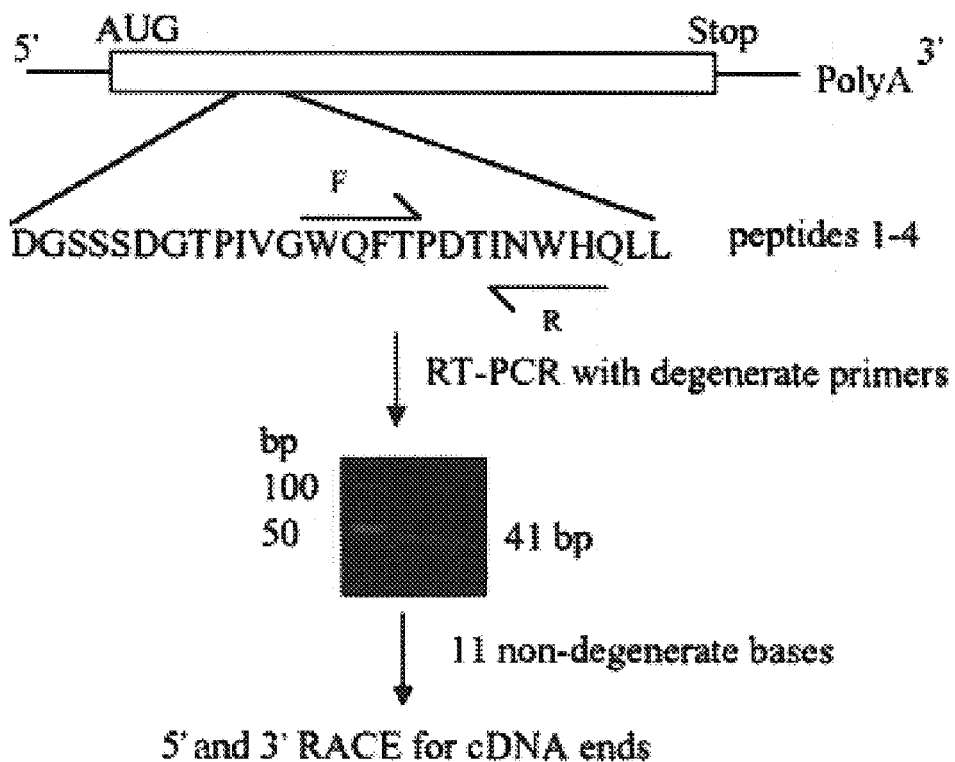
FIG. 13 shows the MOA cloning strategy employed. Relative position of degenerate primers with respect to derived sequence from the overlapping peptides 1–4 is shown by arrows labeled F and R. "Reverse transcriptase-polymerase chain reaction (RF PCR) from total *M. oreades* RNA yields a product of the expected size. Subsequent cloning and sequencing confirms the size of the product (41 bp) and that it codes for the intervening amino acids. Sequencing of this product yielded 11 non-degenerate bases. Primers utilizing this non-degenerate sequence were used for 5' and 3' rapid amplification of cDNA ends ("RACE") to generate a full-length sequence.
Figure 14:
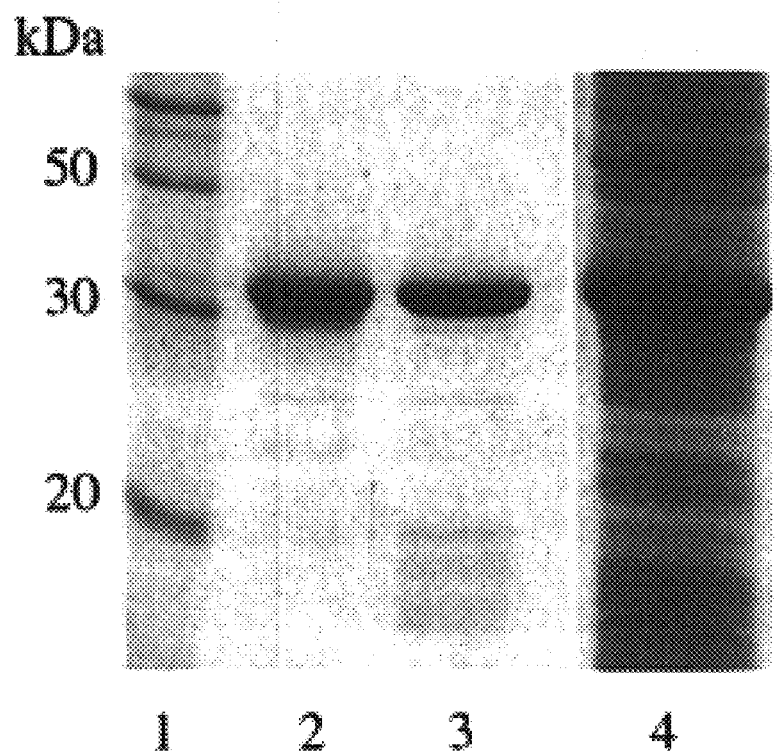
FIG. 14 depicts SDS-PAGE analysis of recombinant MOA. Lane 1 is standard protein ladder. Lane 2 shows native MOA. Lane 3 shows affinity-purified recombinant MOA and Lane 4 shows a lysate of *E. coli* cells expressing recombinant MOA.

Enzymatic digestion, purification of peptide fragments, and degradation of the native protein yielded eight peptide sequences (Table 1). Inspection of the peptide sequences reveals that four are overlapping and likely to originate from a common region. These have been designated peptides 1 through 4. The two low degeneracy oligonucleotides used for RT-PCR are designed from this region (FIG. 13). These oligonucleotides were used to obtain a 41 base pair product whose sequence generated 11 unambiguous bases. The 11 nucleotides between the primer pair proved a sufficient starting point for the generation of a full-length sequence via 5' and 3' RACE. Cloning and sequencing of the 5' and 3' RACE products generated 169 bp and 881 bp of 5' and 3' sequence, predicting a total message size, not including polyadenylation, of 1062 bp (GenBank accession # AY06613). This corresponds well with Northern analysis showing a major brand at ~1.5 kb and aminor band at ~1.1 kb (data not shown). Sequencing of multiple clones reveals that the mRNA apparently contains four nucleotide polymorphisms, only one of which confers an amino acid ambiguity. Specifically, position 200 can be either aspartic acid or asparagine (FIG. 1A). This polymorphism seems unlikely to alter binding specificity as it lies outside of the predicted ricin domain.

Analysis of the cDNA [SEQ ID NO: 1] indicates an open reading frame encoding a protein of 293 amino acids [SEQ ID NO: 2] (FIG. 1A). Inspection of the predicted amino acid sequence shows the presence of all eight of the sequenced peptides. MOA also apparently lacks a signal peptide and is therefore probably cytosolic. The predicted molecular weight of this protein is 32,299. This is consistent with analysis of the native protein by MALDI-TOF mass spectrometric analysis giving a molecular mass for the full-length native protein of 32,290. The initial isolation of MOA from *M. oreades* generated a major protein of 33 kDa and protein fragments of 23 and 10 kDa. Mass spectrometric analysis of the native protein and the fragments, as well as the tryptic digests of these proteins showed remarkable correlation between the observed molecular weights and those predicted from the deduced amino acid sequence (Table 5). This indicates that the isolated lectin and the cloned cDNA product are the same protein.

The MOA open reading frame was cloned into a T7 expression vector. The protein was produced in *E. coli* and purified as described above. Recombinant MOA has an electrophoretic mobility in SDS-PAGE identical to that of native protein at 32 kDa (FIG. 14), and elutes as a single, symmetrical peak at the same elution volume as native MOA from a G2000 SWXL molecular sieve column. Moreover, a polyclonal rabbit antiserum prepared against the native MOA formed precipitin bands of identity with the native and recombinant MOA preparations. The recombinant protein and native protein were also subjected to MALDI-TOF mass spectrometry. Recombinant MOA (rMOA) showed a molecular mass of 32,090±17. Both the native and recombinant proteins were found to contain less than 0.25 mole of neutral sugar per mole of 32 kDa protein by the phenol-sulfuric acid assay, provided that the proteins were purified by absorption to Synsorb B and elution at high pH with diaminopropane, a procedure not involving elution with a sugar. Similarly, neither protein was stained on an SDS-PAGE gel by the periodate-Schiff stain. Since the native protein appears to be blocked at the N-terminus, the difference in the molecular mass of the native vs recombinant proteins might be caused by the presence of a blocking group, such as an N-acetyl moiety (M=42 Da) on the native protein.

Binding constants of several relevant oligosaccharides to recombinant and intact native MOA were determined calorimetrically. As shown in Table 6, little or no difference is observed between the two intact preparations, both of which show slightly stronger binding to Ga1α1,3-linked oligosaccharides than does the proteolyzed ("clipped") form of the native lectin.

Blast searches of the MOA sequence showed highest homology to the ricin domains of a xylanase-arabinofuranosidase from *Streptomyces chattanoogensis* (NCB accession # AAD32559), the beta-mannanase from Polyangium cellulosum (NCB accession # AAK19890, the alpha chain of coagulation factor G from horseshoe crab (accession # BAA04044), and mosquitocidal toxin 21 from *Bacillus sphaericus* (accession # S27514). The presence of a ricin domain is best shown by the alignment of MOA with this subset of ricin domain-containing proteins (FIG. 1B). Other ricin domain-containing proteins showed less homology. Outside of the prospective ricin domain, however, no convincing homology was observed with these or any other known proteins.

TABLE 1

Sequences of *M. oreades* lectin peptides

| Peptide | Sequence | |
|---|---|---|
| 1 | DGSSSDGTPIVG | SEQ ID NO: 9 |
| 2 | DGTPIVGWQFTP | SEQ ID NO: 10 |
| 3 | QFTPDTINNH | SEQ ID NO: 11 |
| 4 | DTINWHQLL | SEQ ID NO: 12 |
| 5 | EAQAAIARNPHIHGTYRGY | SEQ ID NO: 13 |
| 6 | M(G/A)ADSXK | SEQ ID NO: 14 |
| 7 | DLYNGSSEAGTAVNG | SEQ ID NO: 15 |
| 8 | IAGXTGT | SEQ ID NO: 16 |

Ambiguous residues are underlined
X = no residue identified

TABLE 2

Agglutination of Cells by *Marasmius oreades* lectin

| Lectin prep.[1] | Cell type[2] | Observed titre[3] | Protein conc.[4], μg/ml |
|---|---|---|---|
| Crude extract | Human A | 2 | nd* |
| | Human B | 64 | |
| | Human O | 4 | |
| | Rabbit | 64 | |
| Purified | Human A | NA⁺ | >1000 |
| | Human B | 640–1280 | 1.1–2.2 |
| | Human O | 16 | 35 |
| | Rabbit | 640–1280 | 1.1–2.2 |
| | Sheep (trypsin) | NA | >1000 |
| | Pig (fresh) | 80 | 8.8 |
| | EAT[5] (fresh) | 128 | 14 |

[1]Crude extract prepared as described. Purified lectin after treatment with Synsorb A, at 2.9 mg/ml.
[2]Erythrocytes without enzymatic treatment, formaldehyde stabilized, unless otherwise stated.
[3]Maximum dilution of original preparation giving visible agglutination.
[4]Concentration of lectin in final agglutination reaction (60 μL) at end point.
[5]Cultured Ehrlich ascites tumor cells.
*nd—not determined.
⁺NA—no detectable agglutination.

TABLE 3

Thermodynamic parameters of carbohydrate binding to *Marasmius oreades* lectin

| Saccharide | MOA conc. mM[1] | Binding sites, n[2] | Kd, mM | Ka, $10^3$ M$^{-1}$ | $-\Delta H$[2] kCal/mol | $-\Delta G$ kCal/mol | $T\Delta S$ kCal/mol |
|---|---|---|---|---|---|---|---|
| Me-α-Gal | 0.10 | [1.0] | 8.13 | 0.123 | 5.88 | 2.82 | 3.06 |
| Lactose | .084 | 1.02 | 5.08 | 0.197 | 8.86 | 3.1 | 5.76 |
| LacNAc | .092 | 0.99 | 3.45 | 0.290 | 14.22 | 3.33 | 10.9 |
| LactoNbioseβMe | .084 | 1.01 | 4.67 | 0.214 | 6.64 | 3.15 | 3.49 |
| Galβ1,6Gal | .08 | 1.01 | 3.74 | 0.268 | 6.12 | 3.28 | 2.84 |
| Galβ1,2Gal | 0.10 | — | >10 | <0.1 | — | — | — |
| Galβ1,3Gal | 0.10 | [1.0] | 0.182 | 5.48 | 20.1 | 5.05 | 15.0 |
| Galβ1,4Gal | 0.10 | — | >10 | <0.1 | — | — | — |
| Galβ1,6Gal | 0.01 | — | >10 | <0.1 | — | — | — |
| Linear B2 trisacc. | 0.095 | 0.95 | 0.103 | 9.753 | 20.6 | 5.39 | 15.2 |
| B trisaccharide | 0.071 | 0.68 | 0.036 | 27.8 | 20.6 | 6.01 | 14.6 |
| 2' Fucosyllactose | 0.115 | 0.99 | 1.83 | .548 | 10.1 | 3.70 | 6.4 |

[1] Based on a MOA mass of 33 kDa
[2] Based on 1 binding site for mono- or oligosaccharide per 33 kDa polypeptide

TABLE 4

Blood Types of Human Volunteers

| Donor | ABO type | Secretor type | Le[a] | Le[b] |
|---|---|---|---|---|
| 1 | A$_1$ | Se[1] | − | + |
| 2 | A$_2$ | Se | − | + |
| 3 | B | Se[2] | − | − |
| 4 | B | Se | − | + |
| 5 | B | Se | − | + |
| 6 | O | Se | − | + |

[1] Denotes Se/Se or Se/se genotype (ABO type-specific substances occur in serum and other secretions). Se assumed based on positive Le[b].
[2] Based on direct assay of Se antigen.

TABLE 5

Masses of protein subunits and their tryptic peptides from *Marasmius oreades* lectin

| 33 kDa Chain | 23 kDa Chain | 10 kDa Chain | Deduced sequence mass | Deduced sequence position |
|---|---|---|---|---|
| Native protein | | | 32299 | 1–293 |
| 32288 | 22411 | 9794 | 22317 | 93–293 |
| 32542 | 22594 | | 9806 | 2–92 |
| | | | 9790 | 1–91 |
| Tryptic digests | | | | |
| 3263 | | | 3259 | 266–293 |
| 2751 | | 2761 | 2756 | 23–47 |
| 2443 | | | 2439 | 179–199 |
| 1953.6 | | 1953 | 1951 | 5–22 |
| 1796.7 | 1796.9 | 1796.4 | 1795 | 6–22 |
| | | | 1795 | 135–150 |
| 1479.4 | 1479.6 | | 1478 | 252–265 |
| 1338.1 | 1338.2 | | 1337 | 93–103 |
| 1094 | 1094 | | 1093 | 170–178 |
| 849.4 | 849.5 | | 848 | 229–235 |
| 785 | 785 | | 784 | 151–155 |

TABLE 6

Comparison of binding of oligosaccharides by native and recombinant *M. oreades* agglutinin.

| | Ka, $10^3$ M$^{-1}$ | | |
|---|---|---|---|
| Ligand | cMOA | nMOA | rMOA |
| LacNAc | 0.29 | 0.38 | 0.67 |
| Galα1,3Gal | 5.48 | 27.3 | 26.7 |
| Galα1,3Galβ1,4GlcNAc | 9.75 | 39.4 | 30.3 |
| Galα1,3Galβ1,4Glc | n.d. | 16.7 | 13.2 |
| Galα1,3[Fucα1,2]Gal | 27.8 | n.d. | 46.1 |

SEQUENCE LISTING

<160> NUMBER OF SEQ ID NOS: 32

<210> SEQ ID NO 1
<211> LENGTH: 1062
<212> TYPE: DNA

-continued

<213> ORGANISM: Marasmius Oreades

<400> SEQUENCE: 1

```
atcgtttctt aacaactctc agctccaagc ctccactact cgtaactaac tgaaaatgtc    60
tctgcgacgc ggaatttacc acatcgagaa tgctggggtt cccagtgcca ttgatctcaa   120
agacggcagc tccagtgacg gcacacctat cgttggctgg cagtttacac agacacgat   180
caactggcat cagctctggc ttgctgaacc aatccccaac gttgctgata cctttaccct   240
ttgcaacctg ttcagcggta cctacatgga tctctacaac ggttcttccg aagcgggcac   300
cgcagtcaat ggttggcaag gaactgcctt tacgaccaat ccccaccagc tctggaccat   360
caagaagtcg agcgacggta cgagctacaa gatccagaat tatggaagta aaaccttcgt   420
cgatcttgtc aatggcgaca gctctgatgg ggccaaaatt gctggatgga ccggcacttg   480
ggatgaaggt aaccctcacc agaaatggta cttcaatagg atgagcgtct ccagcgcgga   540
ggcccaagcg gctatcgcgc gaaaccctca tattcatggg acttacagag atacatcct   600
cgatggagaa tatcttgtcc tccctaacgc tactttcacg cagatttgga agactccgg   660
tcttcctggt agcaaatggc gtgagcaaat ctatgattgc gatgactttg ctatagccat   720
gaaggccgcc gttgggaagt ggggcgccga ctcctggaag gctaatggct cgccatctt   780
ttgtggagtt atgcttggtg tcaacaaggc tggagatgcg gcccatgctt acaacttcac   840
cctcaccaag gaccatgctg acattgtctt ctttgagcct cagaacggtg gataccctgaa  900
cgacattggc tatgacagct acatggcctt ctactgaagg gacgggtgaa aagacctgtt   960
aygatrcgaa atgtacagtc caagagaaaa agacggaaaa aaaccgcgtg taccagatgt  1020
ccgataaaca gtcatatgta taatccagat actcgattta ct                     1062
```

<210> SEQ ID NO 2
<211> LENGTH: 293
<212> TYPE: PRT
<213> ORGANISM: Marasmius Oreades

<400> SEQUENCE: 2

```
Met Ser Leu Arg Arg Gly Ile Tyr His Ile Glu Asn Ala Gly Val Pro
1               5                   10                  15

Ser Ala Ile Asp Leu Lys Asp Gly Ser Ser Asp Gly Thr Pro Ile
            20                  25                  30

Val Gly Trp Gln Phe Thr Pro Asp Thr Ile Asn Trp His Gln Leu Trp
        35                  40                  45

Leu Ala Glu Pro Ile Pro Asn Val Ala Asp Thr Phe Thr Leu Cys Asn
    50                  55                  60

Leu Phe Ser Gly Thr Tyr Met Asp Leu Tyr Asn Gly Ser Ser Glu Ala
65                  70                  75                  80

Gly Thr Ala Val Asn Gly Trp Gln Gly Thr Ala Phe Thr Thr Asn Pro
                85                  90                  95

His Gln Leu Trp Thr Ile Lys Lys Ser Ser Asp Gly Thr Ser Tyr Lys
            100                 105                 110

Ile Gln Asn Tyr Gly Ser Lys Thr Phe Val Asp Leu Val Asn Gly Asp
        115                 120                 125

Ser Ser Asp Gly Ala Lys Ile Ala Gly Trp Thr Gly Thr Trp Asp Glu
    130                 135                 140

Gly Asn Pro His Gln Lys Trp Tyr Phe Asn Arg Met Ser Val Ser Ser
145                 150                 155                 160

Ala Glu Ala Gln Ala Ala Ile Ala Arg Asn Pro His Ile His Gly Thr
```

```
                    165                 170                 175

Tyr Arg Gly Tyr Ile Leu Asp Gly Glu Tyr Leu Val Leu Pro Asn Ala
            180                 185                 190

Thr Phe Thr Gln Ile Trp Lys Asp Ser Gly Leu Pro Gly Ser Lys Trp
            195                 200                 205

Arg Glu Gln Ile Tyr Asp Cys Asp Asp Phe Ala Ile Ala Met Lys Ala
            210                 215                 220

Ala Val Gly Lys Trp Gly Ala Asp Ser Trp Lys Ala Asn Gly Phe Ala
225                 230                 235                 240

Ile Phe Cys Gly Val Met Leu Gly Val Asn Lys Ala Gly Asp Ala Ala
            245                 250                 255

His Ala Tyr Asn Phe Thr Leu Thr Lys Asp His Ala Asp Ile Val Phe
            260                 265                 270

Phe Glu Pro Gln Asn Gly Gly Tyr Leu Asn Asp Ile Gly Tyr Asp Ser
            275                 280                 285

Tyr Met Ala Phe Tyr
            290

<210> SEQ ID NO 3
<211> LENGTH: 293
<212> TYPE: PRT
<213> ORGANISM: Marasmius Oreades

<400> SEQUENCE: 3

Met Ser Leu Arg Arg Gly Ile Tyr His Ile Glu Asn Ala Gly Val Pro
1               5                   10                  15

Ser Ala Ile Asp Leu Lys Asp Gly Ser Ser Asp Gly Thr Pro Ile
            20                  25                  30

Val Gly Trp Gln Phe Thr Pro Asp Thr Ile Asn Trp His Gln Leu Trp
            35                  40                  45

Leu Ala Glu Pro Ile Pro Asn Val Ala Asp Thr Phe Thr Leu Cys Asn
            50                  55                  60

Leu Phe Ser Gly Thr Tyr Met Asp Leu Tyr Asn Gly Ser Ser Glu Ala
65                  70                  75                  80

Gly Thr Ala Val Asn Gly Trp Gln Gly Thr Ala Phe Thr Thr Asn Pro
            85                  90                  95

His Gln Leu Trp Thr Ile Lys Lys Ser Ser Asp Gly Thr Ser Tyr Lys
            100                 105                 110

Ile Gln Asn Tyr Gly Ser Lys Thr Phe Val Asp Leu Val Asn Gly Asp
            115                 120                 125

Ser Ser Asp Gly Ala Lys Ile Ala Gly Trp Thr Gly Thr Trp Asp Glu
130                 135                 140

Gly Asn Pro His Gln Lys Trp Tyr Phe Asn Arg Met Ser Val Ser Ser
145                 150                 155                 160

Ala Glu Ala Gln Ala Ala Ile Ala Arg Asn Pro His Ile His Gly Thr
            165                 170                 175

Tyr Arg Gly Tyr Ile Leu Asp Gly Glu Tyr Leu Val Leu Pro Asn Ala
            180                 185                 190

Thr Phe Thr Gln Ile Trp Lys Asn Ser Gly Leu Pro Gly Ser Lys Trp
            195                 200                 205

Arg Glu Gln Ile Tyr Asp Cys Asp Asp Phe Ala Ile Ala Met Lys Ala
            210                 215                 220

Ala Val Gly Lys Trp Gly Ala Asp Ser Trp Lys Ala Asn Gly Phe Ala
225                 230                 235                 240
```

```
Ile Phe Cys Gly Val Met Leu Gly Val Asn Lys Ala Gly Asp Ala Ala
                245                 250                 255
His Ala Tyr Asn Phe Thr Leu Thr Lys Asp His Ala Asp Ile Val Phe
            260                 265                 270
Phe Glu Pro Gln Asn Gly Gly Tyr Leu Asn Asp Ile Gly Tyr Asp Ser
        275                 280                 285
Tyr Met Ala Phe Tyr
    290
```

<210> SEQ ID NO 4
<211> LENGTH: 147
<212> TYPE: PRT
<213> ORGANISM: Marasmius Oreades

<400> SEQUENCE: 4

```
His Ile Glu Asn Ala Gly Val Pro Ser Ala Ile Asp Leu Lys Asp Gly
1               5                   10                  15
Ser Ser Ser Asp Gly Thr Pro Ile Val Gly Trp Gln Phe Thr Pro Asp
            20                  25                  30
Thr Ile Asn Trp His Gln Leu Trp Leu Ala Glu Pro Ile Pro Asn Val
        35                  40                  45
Ala Asp Thr Phe Thr Leu Cys Asn Leu Phe Ser Gly Thr Tyr Met Asp
    50                  55                  60
Leu Tyr Asn Gly Ser Ser Glu Ala Gly Thr Ala Val Asn Gly Trp Gln
65                  70                  75                  80
Gly Thr Ala Phe Thr Thr Asn Pro His Gln Leu Trp Thr Ile Lys Lys
                85                  90                  95
Ser Ser Asp Gly Thr Ser Tyr Lys Ile Gln Asn Tyr Gly Ser Lys Thr
            100                 105                 110
Phe Val Asp Leu Val Asn Gly Asp Ser Ser Asp Gly Ala Lys Ile Ala
        115                 120                 125
Gly Trp Thr Gly Thr Trp Asp Glu Gly Asn Pro His Gln Lys Trp Tyr
    130                 135                 140
Phe Asn Arg
145
```

<210> SEQ ID NO 5
<211> LENGTH: 137
<212> TYPE: PRT
<213> ORGANISM: Clostridium botulinum

<400> SEQUENCE: 5

```
Lys Ile Ser Pro Ile Leu Asp Arg Asn Lys Val Val Gln Gln Val Asp
1               5                   10                  15
Met Thr Asn Leu Asn Val Asn Leu Tyr Thr Trp Asp Tyr Gly Arg Asn
            20                  25                  30
Gln Lys Trp Thr Ile Arg Tyr Asn Glu Glu Lys Ala Ala Tyr Gln Phe
        35                  40                  45
Phe Asn Thr Ile Leu Ser Asn Gly Val Leu Thr Trp Ile Phe Ser Asn
    50                  55                  60
Gly Asn Thr Val Arg Val Ser Ser Asn Asp Gln Asn Asn Asp Ala
65                  70                  75                  80
Gln Tyr Trp Leu Ile Asn Pro Val Ser Asp Thr Asp Glu Thr Tyr Thr
                85                  90                  95
Ile Thr Asn Leu Arg Asp Thr Thr Lys Ala Leu Asp Leu Tyr Asn Ser
            100                 105                 110
```

-continued

```
Gln Thr Ala Asn Gly Thr Ala Ile Gln Val Phe Asn Tyr His Gly Asp
        115                 120                 125

Asp Asn Gln Lys Trp Asn Ile Arg Asn
    130                 135
```

<210> SEQ ID NO 6
<211> LENGTH: 136
<212> TYPE: PRT
<213> ORGANISM: Bacillus sphaericus

<400> SEQUENCE: 6

```
Ile Ile Arg Asn Tyr Glu Asn Arg Lys Ile Val Leu Asp Leu Ser Asn
1               5                   10                  15

Gly Ser Thr Thr Asp Gly Asn Gly Leu Leu Gly Phe Glu Phe His Gly
            20                  25                  30

Gly Ile Asn Gln Arg Trp Ile Ile Lys Pro Phe Ser Phe Asn Ser Ile
        35                  40                  45

Gln Asp Gly Ile Tyr Gln Phe Met Thr Val Ile Asn Gln Asp Leu Ile
    50                  55                  60

Ala Asp Leu Thr Thr Asn Asn Tyr Thr Ile Ala Thr Lys Thr Asn Asn
65                  70                  75                  80

Tyr Ser Ser Asn Gln Lys Trp Thr Val Thr Tyr Asn Asp Lys Lys Arg
                85                  90                  95

Ala Tyr Lys Ile Arg Asn Leu Gln His Ala His Leu Ser Leu Ala Trp
            100                 105                 110

Asp Ser Asn His Ser Asp Lys Ile Phe Gly Ala Thr Gly Asp Tyr Asp
        115                 120                 125

Asp Gln Tyr Trp Ile Pro Ile Leu
    130                 135
```

<210> SEQ ID NO 7
<211> LENGTH: 135
<212> TYPE: PRT
<213> ORGANISM: Polyangium cellulosum

<400> SEQUENCE: 7

```
Thr Leu Val Gly Val Gln Ser Gly Arg Cys Val Asp Val Pro Gly Arg
1               5                   10                  15

Ser Thr Ala Asp Asp Ile Ala Leu Asn Leu Trp Asp Cys Ser Gly Gly
            20                  25                  30

Thr Asn Gln Gln Phe Arg Phe Glu Ala Val Ser Gly Gly Tyr Tyr Arg
        35                  40                  45

Ile Arg Asn Val Asn Ser Asn Lys Cys Leu Asp Val Arg Gly Ala Ser
    50                  55                  60

Thr Ala Asp Gly Ala Ala Ile Val Gln Tyr Thr Cys His Asn Asn Thr
65                  70                  75                  80

Asn Gln Gln Trp Thr Val Thr Asp Leu Gly Ser Asp Lys Val Arg Ile
                85                  90                  95

Thr Ser Arg Leu Ser Gly Lys Val Ile Asp Ala Tyr Gly Ser Pro Pro
            100                 105                 110

Glu Asn Gly Thr Ala Leu Phe Gln Trp Pro Ser Ser Gly Gly Thr Asn
        115                 120                 125

Gln Gln Phe Thr Leu Arg Ala
    130                 135
```

<210> SEQ ID NO 8
<211> LENGTH: 135

```
<212> TYPE: PRT
<213> ORGANISM: Streptomyces chattanoogenesis

<400> SEQUENCE: 8

Thr Leu Ser Asn Ala Ala Gly Arg Val Leu Asp Glu Pro Ala Gly
1               5                   10                  15

Gln Asn Asp Asn Gly Thr Pro Leu Gln Val Trp Asp Ala Ser Gly Ala
            20                  25                  30

Ser Asn Gln Gln Trp Arg Ala Gly Arg Asn Ser Asp Gly Ser Tyr Thr
        35                  40                  45

Leu Thr Asn Ile Ala Ser Gly Arg Val Leu Asp Glu Pro Ala Asn Arg
    50                  55                  60

Thr Ala Asn Gly Thr Thr Met Thr Val Trp Asp Ala Asn Gly Gly Ala
65              70                  75                  80

His Gln His Trp Lys Ala Arg Gln Asn Ser Asp Gly Thr Tyr Thr Leu
                85                  90                  95

Thr Asn Val Ala Ser Gly Arg Ala Leu Glu Leu Pro Gly Gly Arg Thr
            100                 105                 110

Ala Asn Gly Thr Pro Val Gln Ile Trp Asp Thr Asn Gly Gly Ala Asn
        115                 120                 125

Gln Arg Trp Thr Phe Lys Pro
    130                 135

<210> SEQ ID NO 9
<211> LENGTH: 12
<212> TYPE: PRT
<213> ORGANISM: Marasmius Oreades

<400> SEQUENCE: 9

Asp Gly Ser Ser Ser Asp Gly Thr Pro Ile Val Gly
1               5                   10

<210> SEQ ID NO 10
<211> LENGTH: 12
<212> TYPE: PRT
<213> ORGANISM: Marasmius Oreades

<400> SEQUENCE: 10

Asp Gly Thr Pro Ile Val Gly Trp Gln Phe Thr Pro
1               5                   10

<210> SEQ ID NO 11
<211> LENGTH: 10
<212> TYPE: PRT
<213> ORGANISM: Marasmius Oreades

<400> SEQUENCE: 11

Gln Phe Thr Pro Asp Thr Ile Asn Asn His
1               5                   10

<210> SEQ ID NO 12
<211> LENGTH: 9
<212> TYPE: PRT
<213> ORGANISM: Marasmius Oreades

<400> SEQUENCE: 12

Asp Thr Ile Asn Trp His Gln Leu Leu
1               5

<210> SEQ ID NO 13
<211> LENGTH: 19
```

```
<212> TYPE: PRT
<213> ORGANISM: Marasmius Oreades

<400> SEQUENCE: 13

Glu Ala Gln Ala Ala Ile Ala Arg Asn Pro His Ile His Gly Thr Tyr
1               5                   10                  15

Arg Gly Tyr

<210> SEQ ID NO 14
<211> LENGTH: 7
<212> TYPE: PRT
<213> ORGANISM: Marasmius Oreades
<220> FEATURE:
<221> NAME/KEY: MISC_FEATURE
<222> LOCATION: (2)..(2)
<223> OTHER INFORMATION: The residue at this position is Gly or Ala.
<220> FEATURE:
<221> NAME/KEY: MISC_FEATURE
<222> LOCATION: (6)..(6)
<223> OTHER INFORMATION: The residue at this position is not identified.

<400> SEQUENCE: 14

Met Xaa Ala Asp Ser Xaa Lys
1               5

<210> SEQ ID NO 15
<211> LENGTH: 15
<212> TYPE: PRT
<213> ORGANISM: Marasmius Oreades

<400> SEQUENCE: 15

Asp Leu Tyr Asn Gly Ser Ser Glu Ala Gly Thr Ala Val Asn Gly
1               5                   10                  15

<210> SEQ ID NO 16
<211> LENGTH: 7
<212> TYPE: PRT
<213> ORGANISM: Marasmius Oreades
<220> FEATURE:
<221> NAME/KEY: MISC_FEATURE
<222> LOCATION: (4)..(4)
<223> OTHER INFORMATION: The residue at this position is not identified.

<400> SEQUENCE: 16

Ile Ala Gly Xaa Thr Gly Thr
1               5

<210> SEQ ID NO 17
<211> LENGTH: 44
<212> TYPE: PRT
<213> ORGANISM: Ricinus communis

<400> SEQUENCE: 17

Val Arg Ile Val Gly Arg Asn Gly Leu Cys Val Asp Val Arg Asp Gly
1               5                   10                  15

Arg Phe His Asn Gly Asn Ala Ile Gln Leu Trp Pro Cys Lys Ser Asn
            20                  25                  30

Thr Asp Ala Asn Gln Leu Trp Thr Leu Lys Arg Asp
        35                  40

<210> SEQ ID NO 18
<211> LENGTH: 41
<212> TYPE: PRT
<213> ORGANISM: Ricinus communis

<400> SEQUENCE: 18
```

```
Gly Thr Ile Leu Asn Leu Tyr Ser Gly Leu Val Leu Asp Val Arg Ala
1               5                   10                  15

Ser Asp Pro Ser Leu Lys Gln Ile Ile Leu Tyr Pro Leu His Gly Asp
            20                  25                  30

Pro Asn Gln Ile Trp Leu Pro Leu Phe
            35                  40

<210> SEQ ID NO 19
<211> LENGTH: 45
<212> TYPE: PRT
<213> ORGANISM: Sambucus ebulus

<400> SEQUENCE: 19

Thr Arg Arg Ile Val Gly Arg Asp Gly Leu Cys Val Asp Val Arg Asn
1               5                   10                  15

Gly Tyr Asp Thr Asp Gly Thr Pro Ile Gln Leu Trp Pro Cys Gly Thr
            20                  25                  30

Gln Arg Asn Gln Gln Trp Thr Phe Tyr Asn Asp Lys Thr
            35                  40                  45

<210> SEQ ID NO 20
<211> LENGTH: 41
<212> TYPE: PRT
<213> ORGANISM: Sambucus ebulus

<400> SEQUENCE: 20

Gly Ser Val Val Asn Leu Lys Ser Thr Arg Val Met Asp Val Lys Glu
1               5                   10                  15

Ser Asp Val Ser Leu Gln Glu Val Ile Ile Phe Pro Ala Thr Gly Asn
            20                  25                  30

Pro Asn Gln Gln Trp Arg Thr Gln Val
            35                  40

<210> SEQ ID NO 21
<211> LENGTH: 51
<212> TYPE: PRT
<213> ORGANISM: Marasmius Oreades

<400> SEQUENCE: 21

Ile Tyr His Ile Glu Asn Ala Gly Val Pro Ser Ala Ile Asp Leu Lys
1               5                   10                  15

Asp Gly Ser Ser Ser Asp Gly Thr Pro Ile Val Gly Trp Gln Phe Thr
            20                  25                  30

Pro Asp Thr Ile Asn Trp His Gln Leu Trp Leu Ala Glu Pro Ile Pro
            35                  40                  45

Asn Val Ala
        50

<210> SEQ ID NO 22
<211> LENGTH: 51
<212> TYPE: PRT
<213> ORGANISM: Marasmius Oreades

<400> SEQUENCE: 22

Asp Thr Phe Thr Leu Cys Asn Leu Phe Ser Gly Thr Tyr Met Asp Leu
1               5                   10                  15

Tyr Asn Gly Ser Ser Glu Ala Gly Thr Ala Val Asn Gly Trp Gln Gly
            20                  25                  30

Thr Ala Phe Thr Thr Asn Pro His Gln Leu Trp Thr Ile Lys Lys Ser
```

```
                35                  40                  45
Asp Ser Gly
    50

<210> SEQ ID NO 23
<211> LENGTH: 47
<212> TYPE: PRT
<213> ORGANISM: Marasmius Oreades

<400> SEQUENCE: 23

Thr Ser Tyr Lys Ile Gln Asn Tyr Gly Ser Lys Thr Phe Val Asp Leu
1               5                   10                  15

Val Asn Gly Asp Ser Ser Asp Gly Ala Lys Ile Ala Gly Trp Thr Gly
            20                  25                  30

Thr Trp Asp Glu Gly Asn Pro His Gln Lys Trp Tyr Phe Asn Arg
        35                  40                  45

<210> SEQ ID NO 24
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The n at this position can be any nucleotide.
<220> FEATURE:
<221> NAME/KEY: misc_feature
<222> LOCATION: (15)..(15)
<223> OTHER INFORMATION: The n at this position can be any nucleotide.

<400> SEQUENCE: 24
ggntggcart tyacncc                                                     17

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Gly Trp Gln Phe Thr Pro
1               5

<210> SEQ ID NO 26
<211> LENGTH: 17
<212> TYPE: DNA
<213> ORGANISM: Artificial Sequence
<220> FEATURE:
<223> OTHER INFORMATION: Synthetic

<400> SEQUENCE: 26
arytgrtgcc arttdat                                                     17

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Ile Asn Trp His Gln Leu
1               5
```

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
arytgrtgcc arttratcgt                                         20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
tgccarttra tcgtgtctgg                                         20

<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The n at this position can be any nucleotide.

<400> SEQUENCE: 30
ggntggcart tyacrccaga                                         20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
carttyacrc cagacacgat                                         20

<210> SEQ ID NO 32
<211> LENGTH: 26
<212> TYPE: PRT
<213> ORGANISM: Marasmius Oreades

<400> SEQUENCE: 32

Asp Gly Ser Ser Ser Asp Gly Thr Pro Ile Val Gly Trp Gln Phe Thr
1               5                   10                  15

Pro Asp Thr Ile Asn Trp His Gln Leu Leu
            20                  25

What is claimed is:

1. A method of detecting a glycoconjugate, comprising:
   a) providing:
      (i) a composition comprising labeled *M. oreades* agglutinin, and
      (ii) a sample obtained from a subject; and
   b) contacting said sample with said labeled *M. oreades* agglutinin under conditions such that a glycoconjugate in said sample is detected.

2. The method of claim 1, wherein said subject has one or more symptoms of malaria.

3. The method of claim 1, wherein said sample is a human blood sample.

4. The method of claim 3, wherein said human blood sample comprises *Plasmodium falciparum* merozoites.

5. The method of claim 1, wherein said labeled *M. oreades* agglutinin comprises a fluorescent label.

6. The method of claim 5, wherein said fluorescent label is fluorescein.

* * * * *